(12) United States Patent
Sayler et al.

(10) Patent No.: US 10,595,744 B2
(45) Date of Patent: Mar. 24, 2020

(54) SURGICAL TOOL-POSITIONING DEVICES AND RELATED METHODS

(71) Applicant: MRI Interventions, Inc., Irvine, CA (US)

(72) Inventors: David John Sayler, Portland, OR (US); Peter Piferi, Orange, CA (US)

(73) Assignee: MRI Interventions, Inc., Irvine, CA (US)

( * ) Notice: Subject to any disclaimer, the term of this patent is extended or adjusted under 35 U.S.C. 154(b) by 418 days.

(21) Appl. No.: 14/619,847

(22) Filed: Feb. 11, 2015

(65) Prior Publication Data

US 2015/0230871 A1 Aug. 20, 2015

Related U.S. Application Data

(60) Provisional application No. 61/939,928, filed on Feb. 14, 2014.

(51) Int. Cl.
| | |
|---|---|
| *A61B 5/00* | (2006.01) |
| *A61B 5/055* | (2006.01) |
| *A61B 6/04* | (2006.01) |
| *A61B 90/57* | (2016.01) |
| *A61B 90/14* | (2016.01) |
| *A61B 90/50* | (2016.01) |
| *A61B 6/03* | (2006.01) |
| *A61B 90/11* | (2016.01) |

(52) U.S. Cl.
CPC .......... *A61B 5/0555* (2013.01); *A61B 5/6835* (2013.01); *A61B 5/702* (2013.01); *A61B 6/0421* (2013.01); *A61B 90/14* (2016.02); *A61B 90/50* (2016.02); *A61B 90/57* (2016.02); *A61B 6/032* (2013.01); *A61B 90/11* (2016.02); *A61B 2505/05* (2013.01)

(58) Field of Classification Search
CPC .. A61G 13/121; A61G 13/128; A61G 13/129; A61G 7/072; A61G 13/12; A61G 13/1202; A61G 13/1285; A61G 13/1295; A61B 5/055; A61B 5/0555; A61B 5/702; A61B 5/3707; A61B 6/0421; A61B 6/032; A61B 6/035; A61B 6/501; A61B 90/11–18; A61B 90/10; A61B 90/50; A61B 2090/571; A61B 2090/3983; A61B 2090/101; A61B 2090/103; A61B 90/14; A61B 90/57; A61B 34/20; A61B 17/60; A61B 19/00; A61B 3/00; A61B 3/0083; A61B 3/13–135; A61B 6/00; A61B 6/0428; A61B 5/6835; A61B 5/70; A47C 20/02–028

USPC ......... 602/34, 17; 128/845, 846; 606/57, 54, 606/59, 130, 96, 104, 87, 129, 98, 86; 600/411, 461

See application file for complete search history.

(56) References Cited

U.S. PATENT DOCUMENTS 3,072,118 A * 1/1963 Standerwick ...... A61B 17/6433
602/17
3,073,310 A * 1/1963 Mocarski ............... A61B 90/11
606/130

(Continued)

*Primary Examiner* — Keri J Nelson
*Assistant Examiner* — Adam Baker
(74) *Attorney, Agent, or Firm* — Myers Bigel, P.A.

(57) ABSTRACT

The disclosure describes assemblies for use during image-guided procedures and can include turret arms and/or longitudinally extending and laterally extending cooperating devices for holding surgical tools such as trajectory guides.

22 Claims, 18 Drawing Sheets

(56) References Cited

U.S. PATENT DOCUMENTS

| | | | | |
|---|---|---|---|---|
| 3,319,954 A * | 5/1967 | Shevick | A61G 13/12 | 5/622 |
| 4,386,602 A * | 6/1983 | Sheldon | A61B 17/0293 | 600/102 |
| 4,465,069 A * | 8/1984 | Barbier | A61B 6/0421 | 600/436 |
| 4,535,763 A * | 8/1985 | Jaquet | A61B 17/62 | 606/56 |
| 4,979,949 A * | 12/1990 | Matsen, III | A61B 17/15 | 606/53 |
| 5,085,219 A * | 2/1992 | Ortendahl | G01R 33/341 | 324/318 |
| 5,154,723 A * | 10/1992 | Kubota | A61G 13/12 | 600/102 |
| 5,280,427 A * | 1/1994 | Magnusson | A61B 90/11 | 600/407 |
| 5,349,956 A * | 9/1994 | Bonutti | A61B 5/0555 | 5/601 |
| 5,372,597 A * | 12/1994 | Hotchkiss | A61B 17/6425 | 602/20 |
| 5,984,930 A * | 11/1999 | Maciunas | A61B 90/11 | 600/417 |
| 6,138,304 A * | 10/2000 | Lipsky | A61G 13/12 | 5/621 |
| 6,206,885 B1 * | 3/2001 | Ghahremani | A61B 17/1695 | 128/DIG. 26 |
| 6,241,670 B1 * | 6/2001 | Nambu | A61N 5/1048 | 378/138 |
| 7,602,190 B2 | 10/2009 | Piferi et al. | | |
| 8,175,677 B2 | 5/2012 | Sayler et al. | | |
| 8,195,272 B2 | 6/2012 | Piferi et al. | | |
| 8,374,677 B2 | 2/2013 | Piferi et al. | | |
| 8,548,569 B2 | 10/2013 | Piferi et al. | | |
| 2002/0007188 A1 * | 1/2002 | Arambula | A61B 17/1757 | 606/130 |
| 2002/0032927 A1 * | 3/2002 | Dinkler | A61B 6/0442 | 5/601 |
| 2004/0220588 A1 * | 11/2004 | Kermode | A61B 10/0041 | 606/129 |
| 2009/0112084 A1 * | 4/2009 | Piferi | G01R 33/286 | 600/421 |
| 2010/0082040 A1 * | 4/2010 | Sahni | A61B 17/3403 | 606/130 |
| 2010/0139669 A1 | 6/2010 | Piferi et al. | | |
| 2010/0198052 A1 | 8/2010 | Jenkins et al. | | |
| 2011/0213383 A1 * | 9/2011 | Lee | A61B 34/71 | 606/130 |
| 2014/0024925 A1 | 1/2014 | Piferi | | |
| 2015/0031982 A1 | 1/2015 | Piferi et al. | | |
| 2015/0157306 A1 * | 6/2015 | Schuele | A61B 17/02 | 600/227 |

* cited by examiner

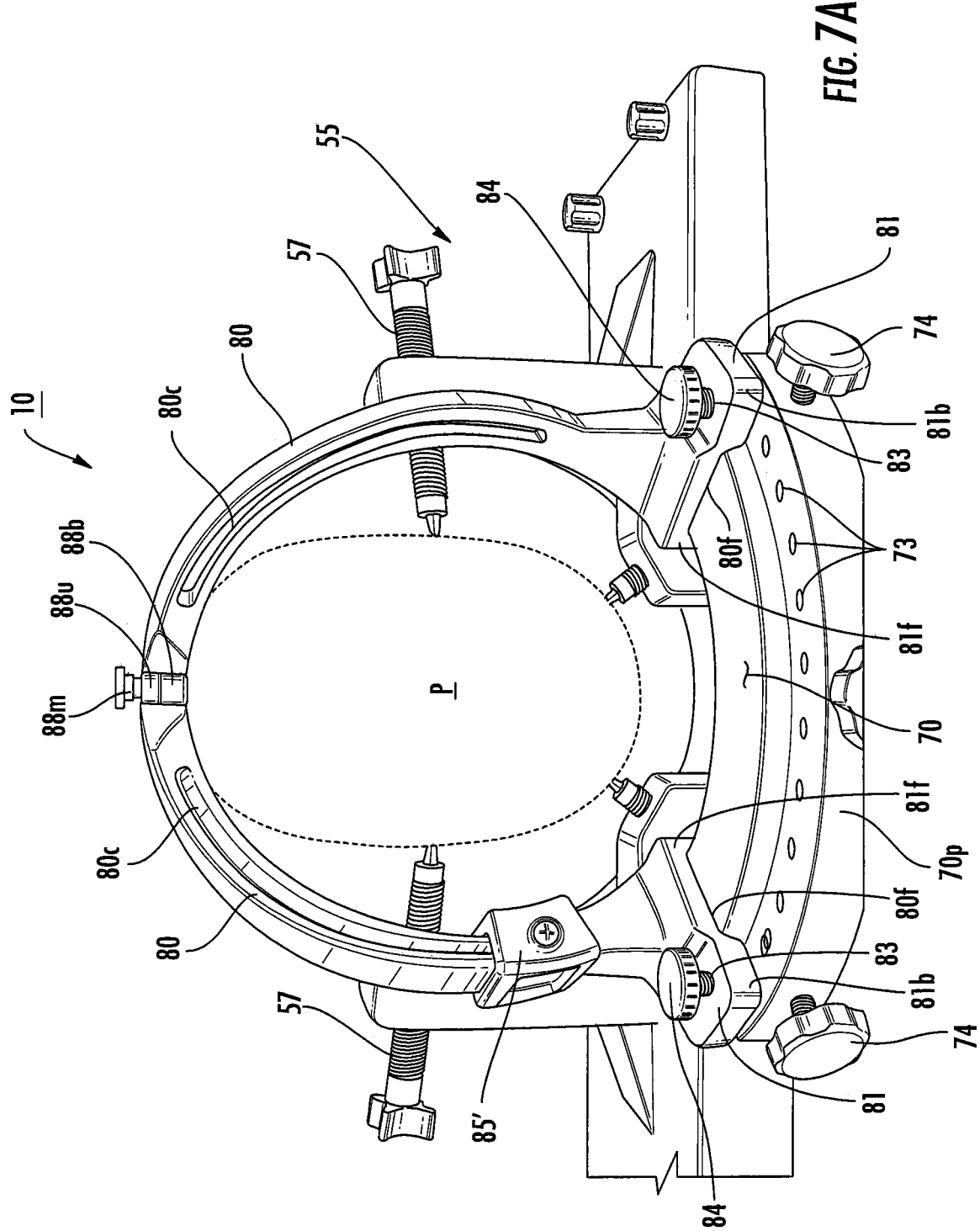

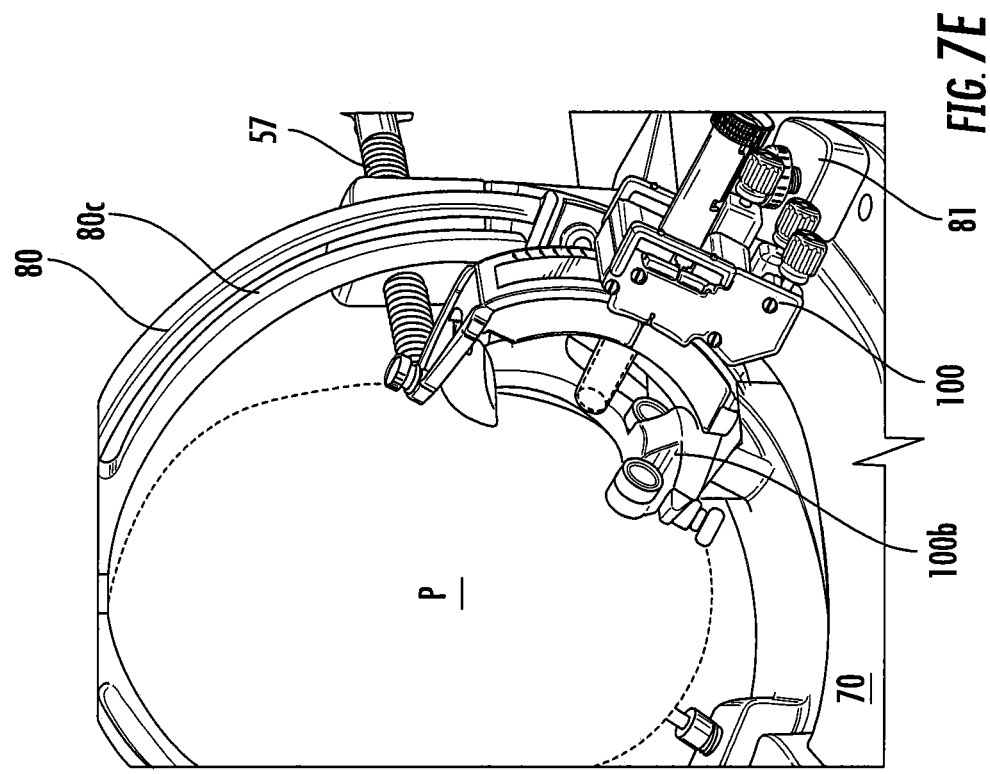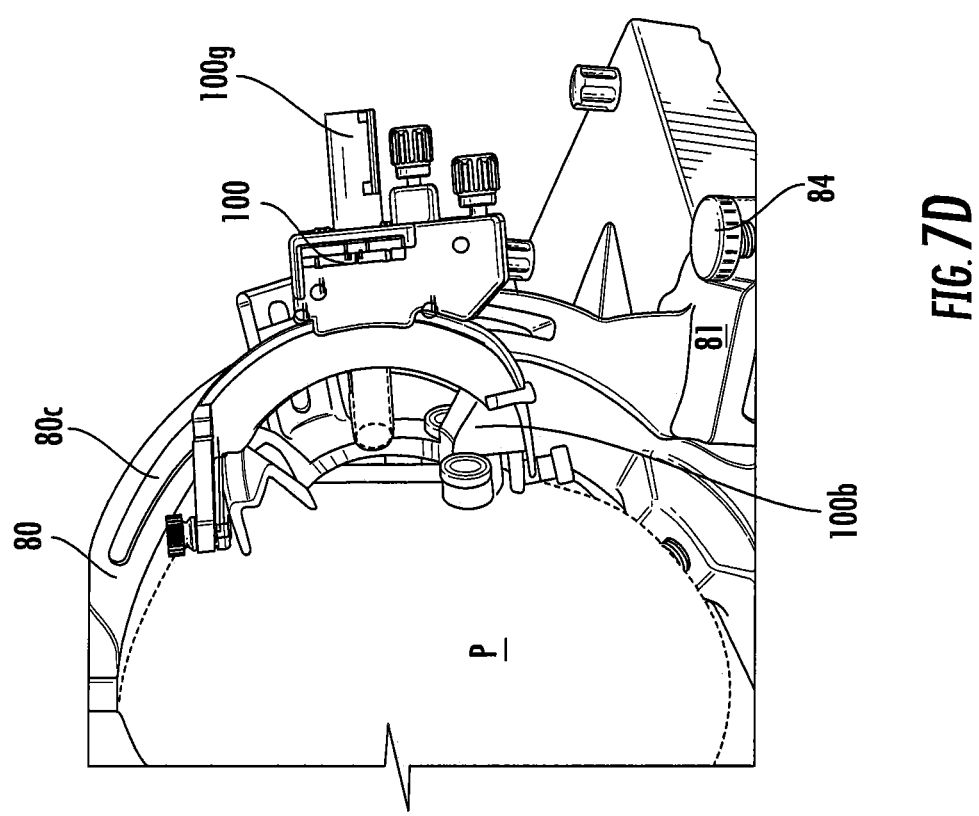

SURGICAL TOOL-POSITIONING DEVICES AND RELATED METHODS

RELATED APPLICATIONS

This application claims the benefit of and priority to U.S. Provisional Application Ser. No. 61/939,928, filed Feb. 14, 2014, the contents of which are hereby incorporated by reference as if recited in full herein.

FIELD OF THE INVENTION

The present invention relates generally to devices used during medical procedures and may be particularly suitable for use in MRI-guided procedures.

BACKGROUND OF THE INVENTION

MRI guided interventional procedures are becoming more viable and may provide improved outcomes, alternative procedures and/or therapies over conventional imaging modalities and procedures.

SUMMARY OF EMBODIMENTS OF THE INVENTION

Embodiments of the invention are directed to surgical devices that can provide external structural support for intrabody surgical devices. The devices may be configured for CT or MRI environments or may be configured to be compatible for both CT and MRI environments.

A surgical frame assembly comprising: (a) at least one turret arm comprising an arcuate segment attachable to a support structure; and (b) a surgical tool moveably attached to the at least one arcuate turret arm so that the surgical tool can be positionally adjusted relative to a target anatomical location of a patient under the arcuate segment of the turret arm.

The surgical tool can be a trajectory guide or can be held by a trajectory guide. The trajectory guide can include a trajectory guide base with an elongate slot. A mounting member can extend through the elongate slot of the trajectory guide to attach the trajectory guide to the arcuate segment of the at least one turret arm so that the trajectory guide can be position adjustable relative to a patient, in X, Y and Z directions.

The trajectory guide can be slidably attached to a respective one of the at least one turret arm so that the trajectory guide can be slidably positioned at different radial positions over a length of the arcuate segment of the turret arm.

The arcuate segment of the at least one turret arm can have a radius of curvature that is between about 100 mm and 150 mm.

The arcuate segment of the at least one turret arm can include an arcuate elongate channel residing between upper and lower outer surfaces of the arcuate segment of the at least one turret arm and a mounting member that engages the arcuate elongate channel to secure the surgical tool into a desired position.

The at least one turret arm includes first and second spaced apart turret arms.

Upper end portions of the first and second turret arms can be configured to be attachable to each other.

The arcuate segment of the at least one turret arm can have a telescoping configuration such that that the arcuate segment has an end that can extend and retract from a lower portion of the turret arm to reside at different height positions.

The frame assembly can include a mount member attached to the arcuate segment of the at least one turret arm. The mount member can be configured to secure the surgical tool (e.g., trajectory guide) to the arcuate segment of the turret arm. The mount member can slidably extend over the arcuate segment and securely attach the surgical tool at a desired location over a at least a major portion of a length of the arcuate segment of the at least one turret arm.

The frame assembly can include a head fixation frame attached to the turret arm. Head fixation members can extend laterally inward on opposing sides of the head fixation frame. The arcuate segment of the at least one turret arm can extend above the head fixation members at a location that is proximate the head fixation members so as to reside over a head of a patient.

The base of the trajectory guide can have a circular shape defining a center overlying a target intrabody entry point of a patient.

The frame assembly can include a turret base. The at least one turret arm can have a lower end portion that resides on an upper surface of the turret base and can be locked into different positions relative to the turret base.

The at least one turret arm can include first and second turret arms. Lower end portions of the first and second turret arms can be independently moveably attachable at different locations of the turret base.

The frame assembly can include a surgical tool base with an outwardly extending turret connection arm and a mount member that attaches the turret connection arm to a respective at least one turret arm to hold the surgical tool base at a desired height location, adjustable relative to the corresponding turret arm.

The surgical tool can include a base with a planar bottom surface with a perimeter. The perimeter can have a radially extending gap space. The surgical tool base can hold a plurality of circumferentially spaced apart fiducials.

The frame assembly can include turret base with a plurality of laterally spaced apart downwardly extending apertures. The at least one turret arm can include a lower support member or configuration that includes a laterally extending slot. The slot can have a length that corresponds to a separation distance between adjacent downwardly extending turret base apertures to thereby allow for various lockable positions.

Other embodiments are directed to methods of preparing for an image-guided surgery. The methods include: providing a head fixation assembly; adjusting a location of at least one turret arm attached to and/or positioned proximate the head fixation assembly to a desired position relative to a patient's head; and attaching a surgical tool to the turret arm.

The method can also include, before the adjusting the location of the at least one turret arm: attaching a hoop mount to the head fixation assembly; attaching a turret base to the hoop mount; then attaching the at least one turret arm to the turret base, then adjusting the location.

The surgical tool can include a trajectory guide primary body with an open cylindrical channel and a trajectory guide base that is releasably attachable to the trajectory guide. The at least one turret arm can include an arcuate segment. The method can include adjusting a height of the trajectory guide base relative to the arcuate segment of the turret arm before attaching the trajectory guide primary body.

Yet other embodiments are directed to a surgical tool positioning assembly. The assembly includes: (i) a first laterally extending cross member; (ii) first and second laterally spaced apart arms extending down from the first laterally extending cross member and residing on laterally opposing end portions of the first cross-member; (iii) first and second mounting members pivotably attached to lower end portions of a corresponding first and second arm, the first and second mounting members attached to opposing longitudinally extending table rails of an imaging scanner; (iv) first and second locking members that adjust an orientation of corresponding first and second arms; (v) a longitudinally extending rod held by the first laterally extending cross member, the rod slidingly moveable in at least a longitudinal direction relative to the first cross member to be able to be moved fore and aft and locked into a desired position; and (iv) a holding member held by an end portion of the rod away from the first cross bar. The holding member is configured to hold at least one surgical tool which is optionally a targeting or guide cannula.

The assembly can also include first and second laterally extending fixation members that mount to respective table rails via clamping members at a longitudinal distance away from the first cross-member.

The fixation members can be head fixation members that can be laterally adjustable to accommodate different size heads.

Further features, advantages and details of the present invention will be appreciated by those of ordinary skill in the art from a reading of the figures and the detailed description of the preferred embodiments that follow, such description being merely illustrative of the present invention. Features described with respect with one embodiment can be incorporated with or into other embodiments although not specifically discussed therewith. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

DETAILED DESCRIPTION OF EMBODIMENTS OF THE INVENTION

Figure 1:
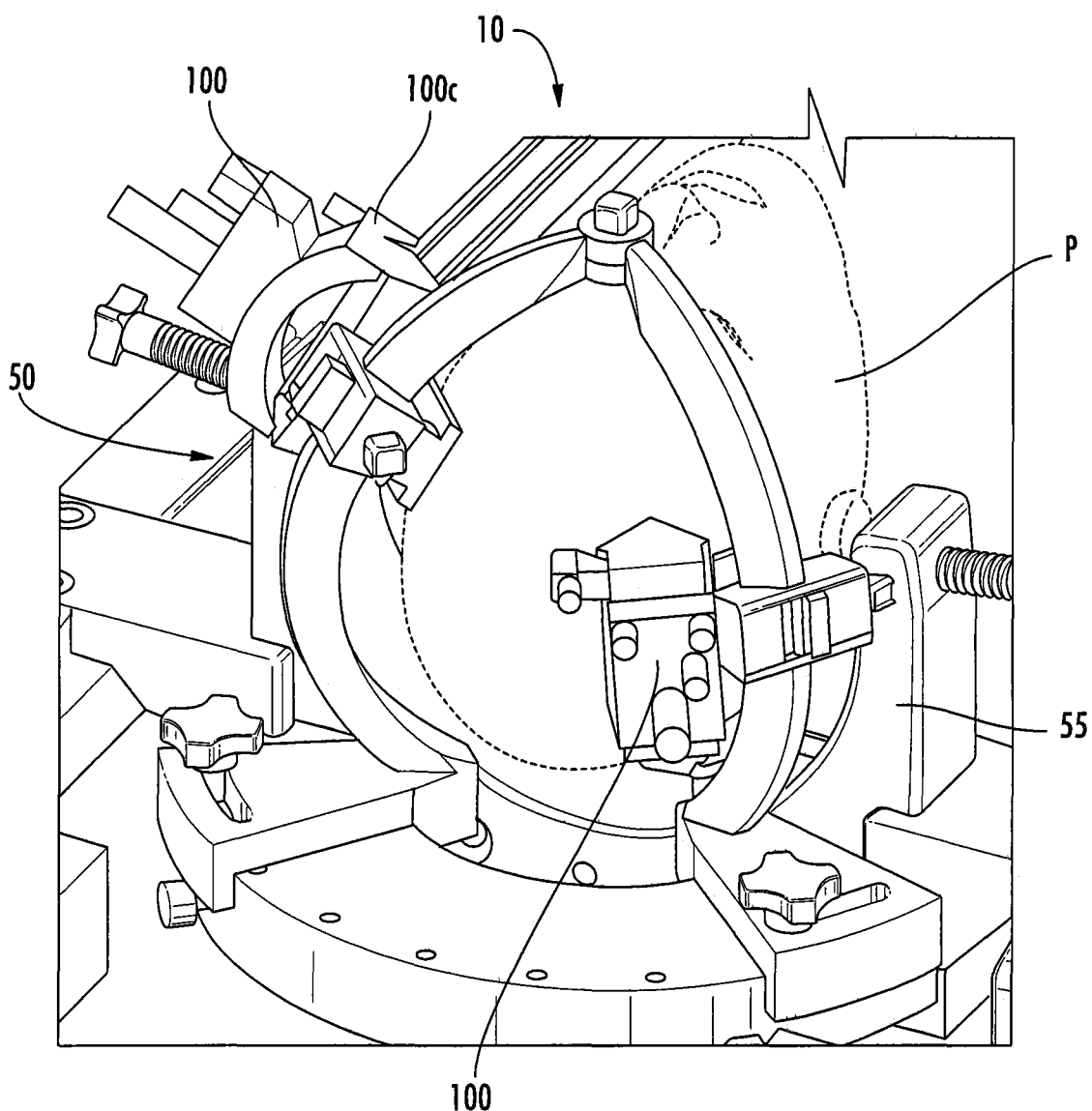
FIG. 1 is a top perspective view of a frame assembly that is configured to be supported by a surgical patient support table according to embodiments of the present invention.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", "supported by" etc., another element, it can be directly on, attached to, connected to, coupled with or contacting the other element or intervening elements may also be present (e.g., indirectly supported, attached, coupled, contacting, connected, coupled, etc. . . . ). In contrast, when an element is referred to as being, for example, "directly on", "directly attached" to, "directly connected" to, "directly coupled" with, "directly supported by" or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

The term "about" with respect to a number indicates that the value may vary between +/−20%.

The term "scanner bed" is used interchangeably with "table" and refers to a patient support surface or frame thereof (which is typically relatively rigid) that, in operative position, resides in a scanner, such as a CT or MRI scanner. For MRI use, the scanner bed resides in a region of a homogeneous high magnetic field associated with a Magnetic Resonance Imaging (MRI) scanner during active image signal acquisition. The scanner bed can typically translate in a longitudinal direction to position the patient in the homogeneous magnetic field region of the magnet. MRI scanners are well known to those of skill in the art and include, for example, the SIGNA 1.5T/3.0T from GE Healthcare: the ACHEIVA 1.5T/3.0T and the INTEGRA 1.5T from Philips Medical System; and the MAGNETOM Avanto, the MAGNETOM Espree, the MAGNETOM Symphony, and the MAGNETOM Trio, from Siemens Medical. CT Scanners are also well known in the art.

The term "MRI-compatible" means that a device is safe for use in an MRI environment that can operate as intended in an MRI environment and not introduce artifacts into MRI images. As such, if residing within the high-magnetic field region of the magnet, the MRI-compatible device is typically made of a non-ferromagnetic material(s) suitable to reside and/or operate in a high magnetic field environment.

The term "high magnetic field" refers to magnetic fields above 0.5 T, typically between 1.5 T to 10 T.

The term "tool" refers to devices that facilitate medical procedures.

The term "turret arm" refers to an upwardly or outwardly projecting structure (relative to a base or other structural support) that can hold and/or partially or totally support at least one medical tool.

Embodiments of the invention are particularly suitable for veterinarian or human therapeutic or diagnostic use, but may be used for research or other purposes.

The term "sterile" and derivatives thereof means that the component meets regulatory clinical cleanliness standards for medical procedures.

The term "wide range of motion" refers to support arms that can take on many different shapes to reside over desired anatomical entry sites into the body.

The term "fiducial marker" refers to a marker that can be electronically identified using image recognition and/or electronic interrogation, typically interrogation of CT or MRI image data. The fiducial marker can be provided in any suitable manner, such as, but not limited to, a geometric shape, a component on or in the device, optical or electrical tracking coils, a coating or fluid-filled component or feature (or combinations of different types of fiducial markers) that makes the fiducial marker(s) MRI-visible or CT visible with sufficient signal intensity (brightness) for identifying location and/or orientation information for the device and/or components thereof in space.

Embodiments of the present invention can be configured to carry out or facilitate CT or MRI guided procedures, including, for example diagnostic and interventional procedures such as to guide and/or place interventional devices to any desired internal region of the body or object, including deep brain sites for neurosurgeries or other target intrabody locations for other procedures. The object can be any object, and may be particularly suitable for animal and/or human subjects. For example, the system and/or devices thereof can be used for gene, e.g., antibody, and/or stem-cell based therapy delivery or other therapy delivery to intrabody targets in the brain, heart, lungs, liver, kidney, ovary, stomach, intestine, colon, spine or to other locations. In addition, embodiments of the systems can be used to treat cancer sites. In some embodiments, the systems can be used to ablate tissue and/or delivery pharmacologic material in the brain, heart or other locations. In some embodiments, it is contemplated that the systems can be configured to treat AFIB, deliver stem cells or other cardio-rebuilding cells or products into cardiac tissue, such as a heart wall, via a minimally invasive MRI guided procedure while the heart is beating (i.e., not requiring a non-beating heart with the patient on a heart-lung machine).

Figure 2:
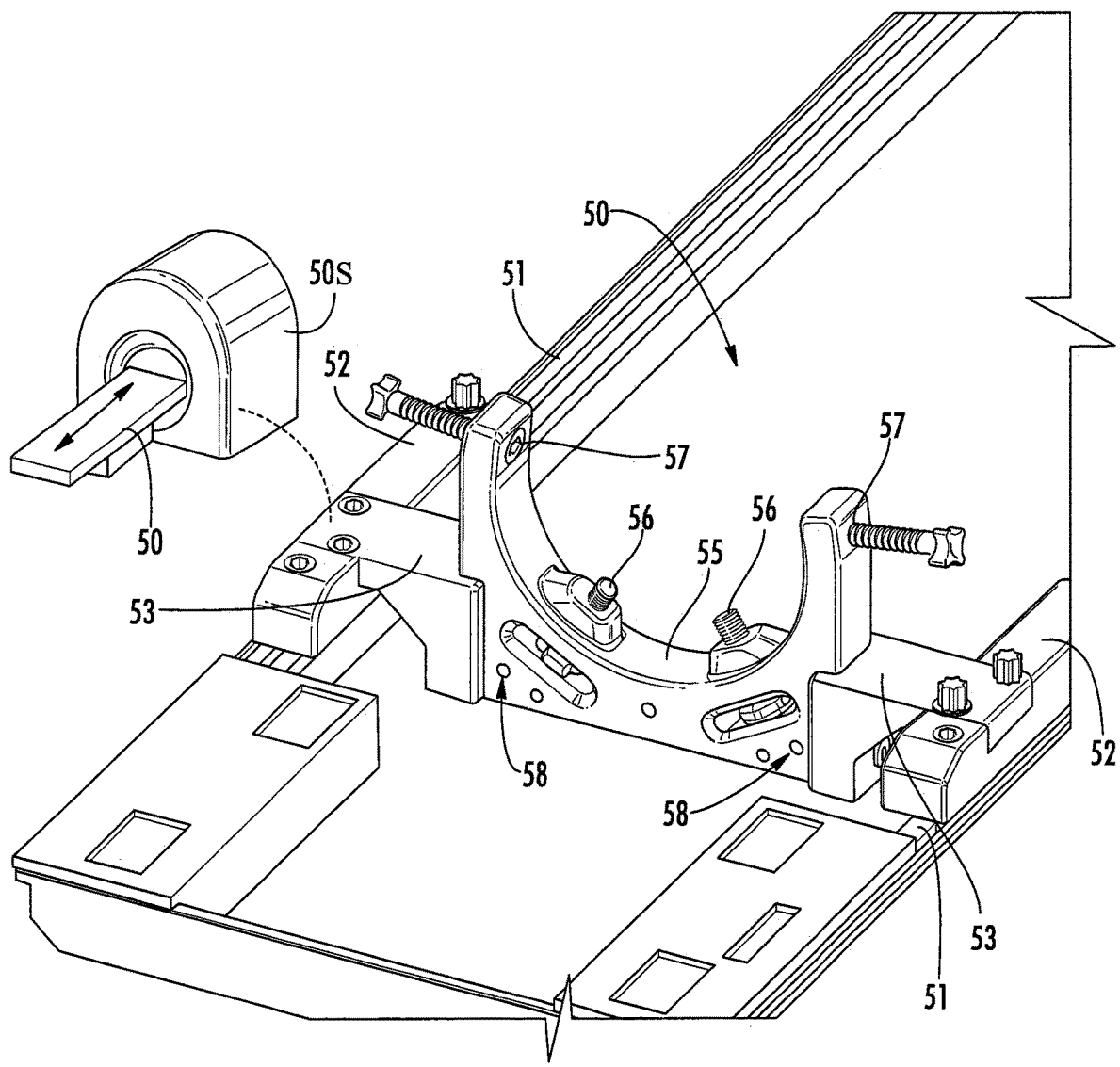
FIG. 2 is an enlarged end perspective view of a (subject/patient) fixation frame component of the assembly shown in FIG. 1 according to embodiments of the present invention.

Referring now to the figures, FIGS. 1 and 2 illustrate an example of a frame assembly 10 attached to a scanner table or bed 50 of an MRI, CT or other imaging scanner 50S. The frame assembly 10 is configured to support at least one surgical tool 100 relative to a patient P.

The tool 100 can comprise a trajectory guide 100g (FIG. 7D) with or without a targeting cannula 100c (FIG. 1) for allowing components such as catheters, needles, leads with electrodes, drill bits, fluid delivery cannulae, or other devices to be inserted into a patient's body along a desired intrabody path through the cannula and/or guide. The tool 100 can reside on or above a patient. The tool 100 can reside against/on an outer surface of a patient or a surface that is made visible for the surgical procedure. In some embodiments, the tool 100 may directly or indirectly attach to the patient such as with screws to a frameless stereotactic frame attached to bone, adhesives or other attachment means, typically positioned over a target intrabody target surgical site.

Referring to FIGS. 1 and 2, the frame assembly 10 can optionally include and/or attach to a patient fixation frame 55 that can includes fixation members 56, 57 (typically threaded members such as sterile screws). The fixation frame 55 can be a head fixation frame for neurological/brain surgeries but may be configured for other anatomical targets such as a torso, leg, arm, chest, hand, foot, finger, toe and the like. The fixation frame 55 can cooperate with RF coils to obtain MRI signals. For additional description of suitable head fixation frames, see, e.g., U.S. Pat. No. 8,548,569, the contents of which are hereby incorporated by reference as if recited in full herein. However, the frame assembly 10 may attach to other support surfaces/structures.

The fixation frame 55 can include transversely extending attachment members 53 that merge into or attach to longitudinally extending frame members 52 that attach to upwardly extending rails 51 of the scanner table or bed 50. The longitudinally extending frame members 52 and the transversely extending members 53 can have a unitary body (e.g., a monolithic single, molded, cast or machined component) or may be formed of multiple attachable components as shown.

Figure 3:
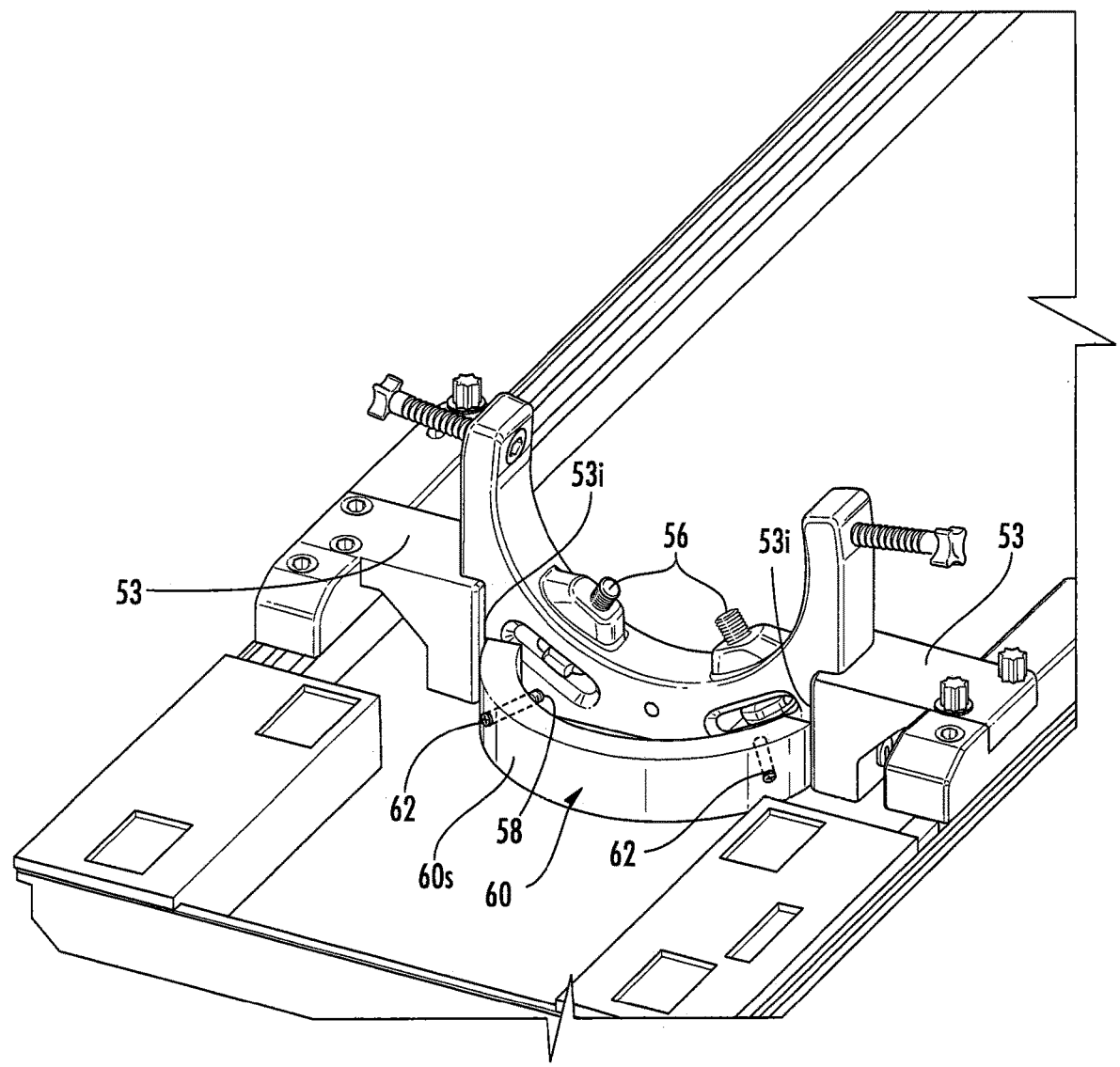
FIG. 3 is an enlarged end perspective view of a hoop mount of the frame assembly shown in FIG. 1, attached to the fixation frame shown in FIG. 2, forming a frame subassembly according to embodiments of the present invention.

FIG. 3 illustrates that a hoop mount 60 can be attached to the fixation frame 55. The hoop mount 60 can be attached using attachment members 62 that extend through apertures 58 (FIG. 2) associated with the fixation frame that reside below and laterally offset from the lower fixation members 56. The hoop mount 60 can have an arcuate perimeter shape and reside adjacent inner ends 53i of the transverse members 53. However, the hoop mount 60 can have other shapes and/or sizes. The hoop mount 60 can have blind channels that accommodate the attachment members 62 so that an external surface 60s of the hoop mount is smooth. In other embodiments, the attachment members 62 can be flush or recessed into the outer surface 60s. The fixation frame 55 and hoop mount 60 can define a subassembly 65 of the frame assembly 10.

In other embodiments, the frame assembly 10 can exclude the fixation frame 55 and/or hoop mount 60. Thus, the frame assembly 10 can include (only) the one or more turret arms 80 attached to any suitable support or structure to position a respective surgical tool 100 with or without a trajectory guide and/or targeting cannula.

Figure 4A:
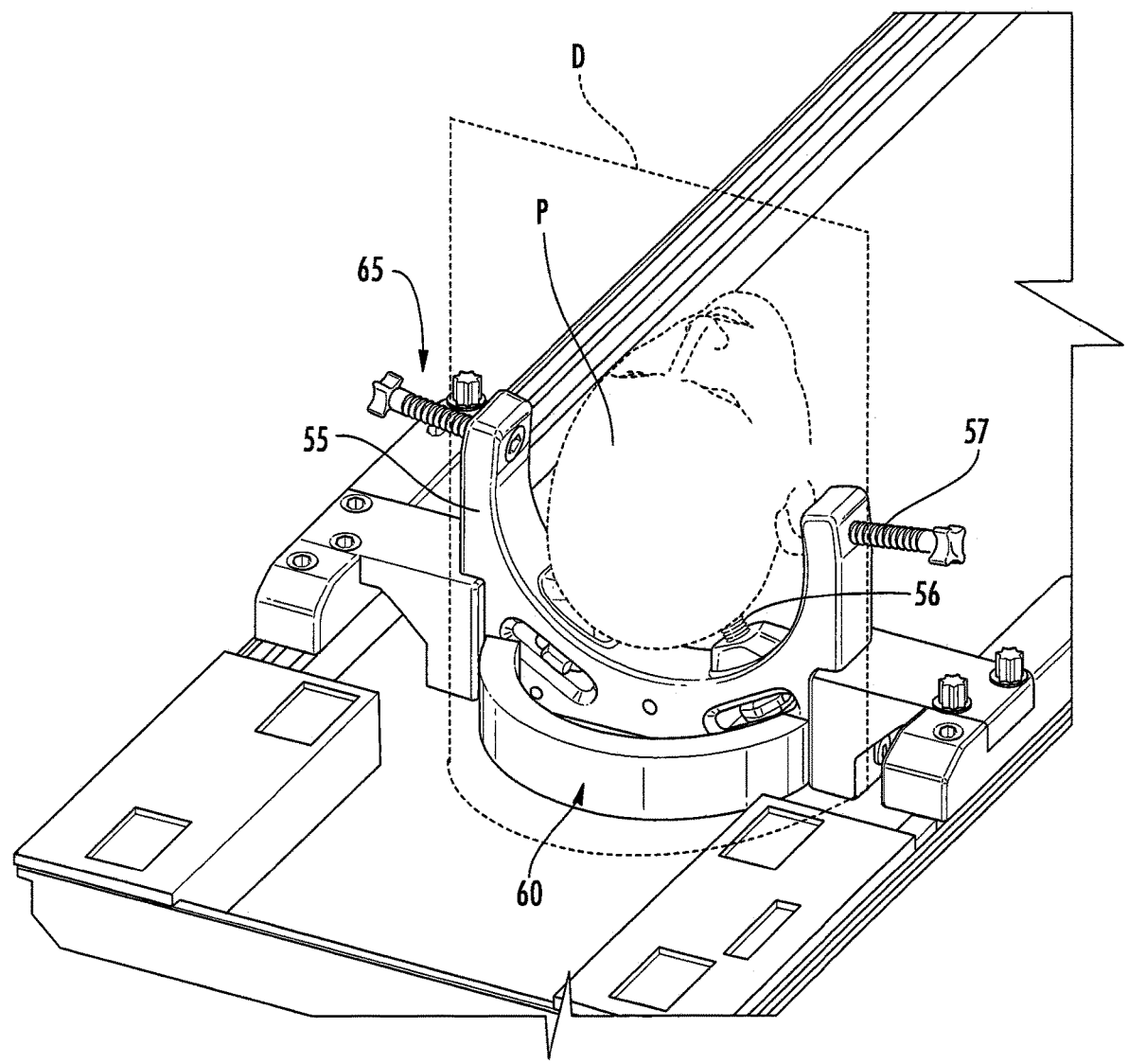
FIG. 4A is an end perspective view of the subassembly shown in FIG. 3, schematically illustrating a patient secured to the fixation frame according to embodiments of the present invention.
Figure 4B:
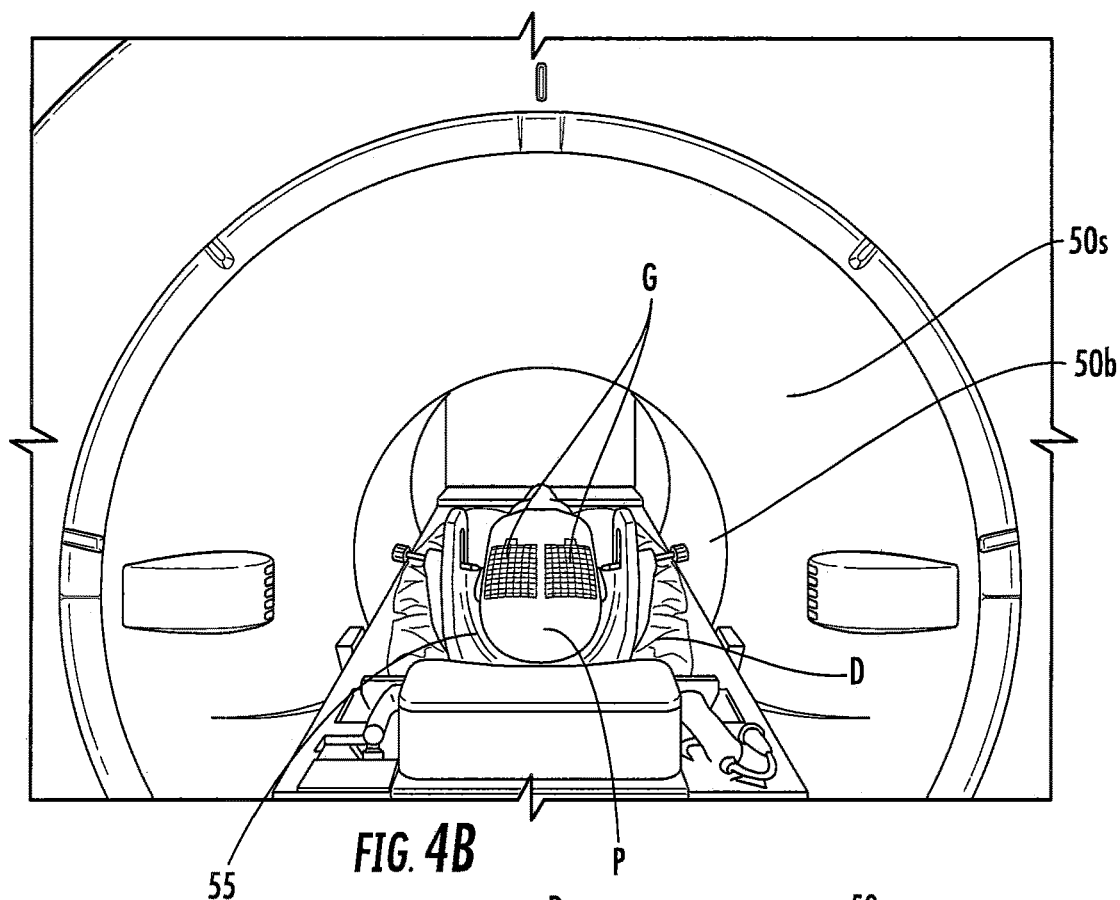
FIGS. 4B and 4C are end perspective views of a Scanner with a surgical drape positioned relative to the frame assembly according to some embodiments of the present invention.
Figure 4C:
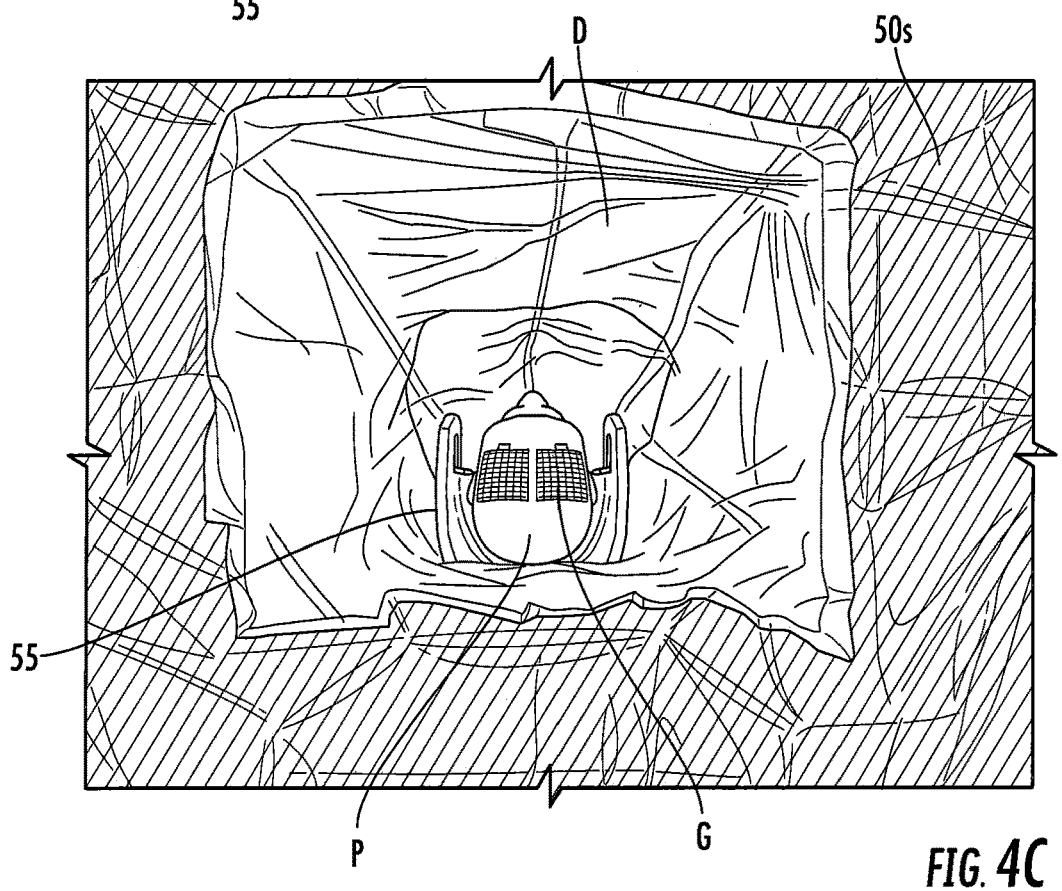

FIG. 4A illustrates that, in some embodiments, a patient P can be secured to the fixation frame 55 after the hoop mount 60 is in place and attached to the fixation frame 55 to form the subassembly 65, and before other components of the frame assembly 10 are attached. For example, in the embodiment shown, the patient's head is secured to the fixation frame 55 using the upper and lower fixation members 57, 56. A surgical drape D can be placed over the patient's head to define a sterile separation space for the surgery as shown schematically in FIG. 4A. FIGS. 4B and 4C illustrate the drape D in the Scanner 50S with FIG. 4C illustrating the drape defining the surgical space with respect to the patient inside the bore 50b of the Scanner 50s. See, e.g., U.S. Patent Application Publication Serial Number 2010/0139669 for further discussion of exemplary drapes and uses according to embodiments of the present invention, the contents of which are hereby incorporated by reference as if recited in full herein.

FIGS. 4B and 4C illustrate that placement of the surgical tool 100 and/or components of the frame assembly 10 (e.g., turret arms 80, FIGS. 6A, 6B, 7A) can be facilitated by the use of an MR visible marking grid G placed on the body of the patient P. The marking grid can be used with automated planning software to help define the appropriate trajectory path and target site in the body.

The term "grid" refers to a pattern of crossed lines or shapes used as a reference for locating points or small spaces, e.g., a series of rows and intersecting columns, such as horizontal rows and vertical columns (but orientations other than vertical and horizontal can also be used). The grid can include at least one fiducial marker. The grid can include associated visual indicia such as alphabetical markings (e.g., A-Z and the like) for rows and numbers for columns (e.g., 1-10) or the reverse. Other marking indicia may also be used. The grid can be provided as a flexible patch that can be releasably attached to the skin of a patient. For additional description of suitable grid devices, see co-pending, co-assigned U.S. patent application Ser. No. 12/236,621, the contents of which are hereby incorporated by reference as if recited in full herein.

Figure 5A:
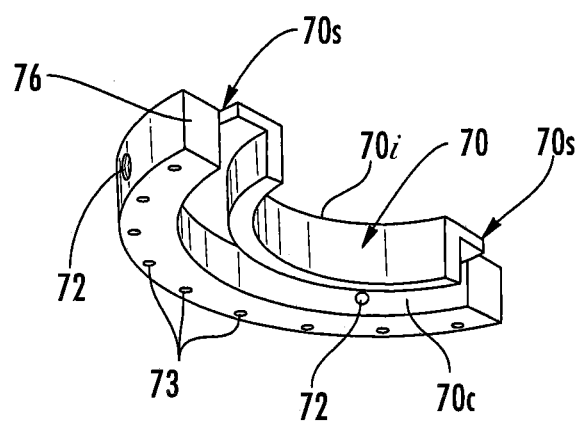
FIG. 5A is a bottom perspective view of a turret base of the frame assembly that is configured to attach to the hoop mount according to embodiments of the present invention.
Figure 5B:
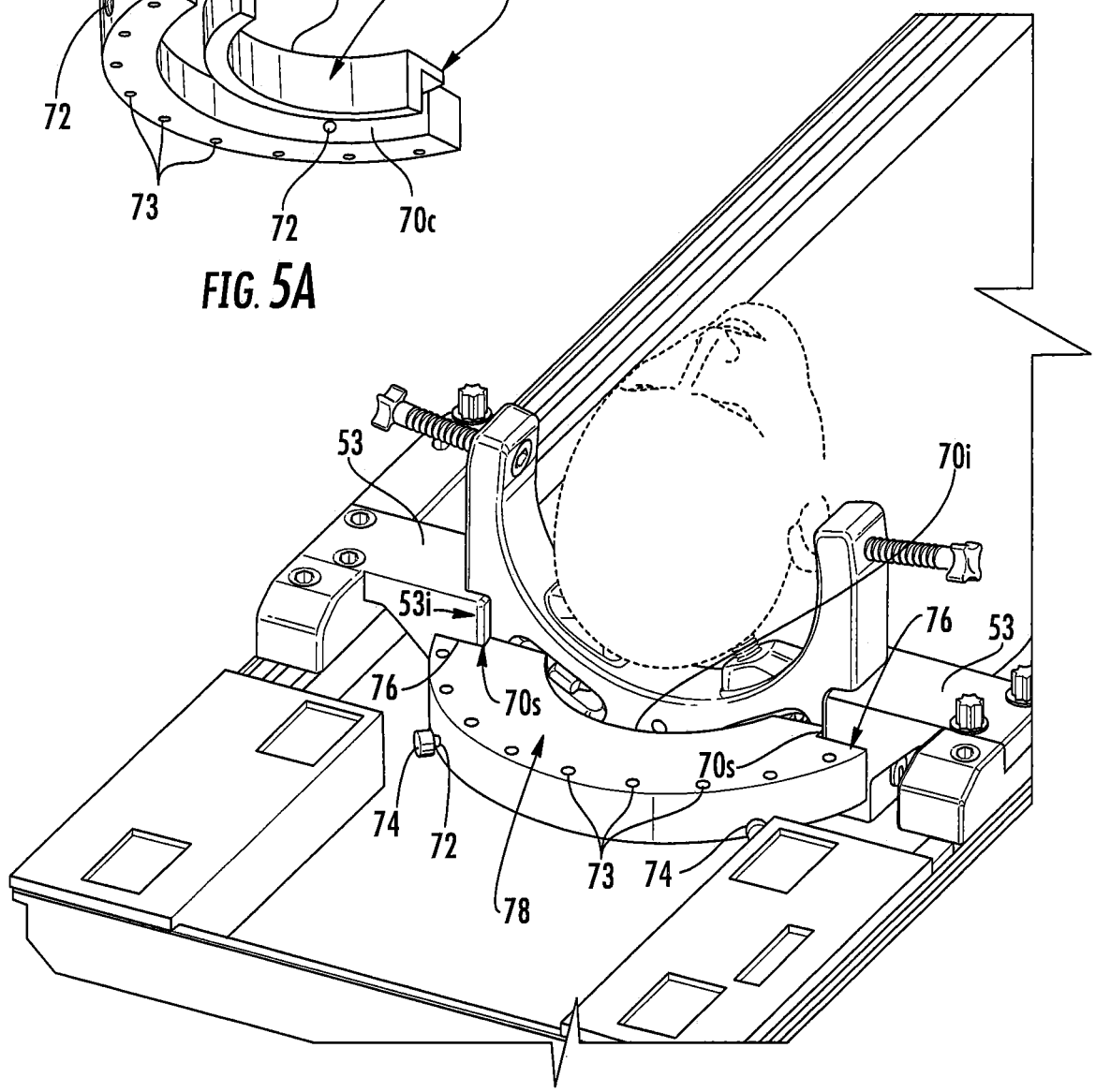
FIG. 5B is an end perspective view of the turret base attached to the hoop mount according to embodiments of the present invention.

FIGS. 5A and 5B illustrate an example of a turret base 70 that can slidably engage a support structure such as a hoop mount 60 (slidably extend down to align the internal channel(s) onto the upper portion of the hoop mount). The turret base 70 can include a downwardly extending arcuate channel 70c that snugly attaches to the hoop mount 60. The arcuate channel 70c can reside under a flat upper surface 78 of the turret base 70. The turret base 70 is configured to adjustably hold at least one turret arm 80 (FIGS. 6A, 6B, 7D, 7E). The turret arms 80 are configured to hold the surgical tool 100. The at least one turret arm 80 and turret base 70 are configured to allow positional adjustment of the tool in at least two dimensions, e.g., X and Z, and typically in three dimensions, e.g., X, Y and Z.

The turret arm(s) 80 can have a length associated with a height dimension that is between about 6-12 inches, in some embodiments. The length can be measured starting at a location just above the turret base 70. In particular embodiments, the turret arm(s) 80 can have a length of between 9-12 inches, including about 9 inches, about 10 inches, about 11 inches and about 12 inches.

In some embodiments, the turret arm(s) 80 can reside closely spaced apart from the fixation members 57, typically within about 0.25 inches to about 4 inches therefrom, which may be particularly useful where head fixation members 57 are used.

The turret base 70 can be configured to attach to the hoop mount 60 and/or directly to the fixation frame 55 or to another support member in any suitable manner to provide structural stability. The hoop mount 60 can have a height that is greater than that of the turret base 70 so that the turret base 70 resides over an upper portion of the hoop mount 60 suspended or held a distance above a patient support table and/or a distance above the lower end of the hoop mount 60. The turret base 70 can have a height that is between 20% to 75% the height of the hoop mount 60. In some embodiments, the turret base 70 has a height that is between 1-5 inches less than the height of the hoop mount 60.

In the embodiment shown in FIGS. 5A and 5B, the turret base 70 can include a plurality of upwardly extending, circumferentially spaced apart, through-apertures 73 and radially extending apertures 72. These apertures 73 can reside about an outer perimeter of the base 70 in a direction facing away from the hoop mount 60 and/or patient P. The turret base 70 can be secured to the hoop mount 60 using attachment members 74 that extend through the apertures 72. The turret base 70 can be configured with an inner arcuate perimeter 70i that merges into a stepped region that defines a laterally extending flat segment 76 that abuts the inner end portions 53i of the laterally extending frame members 53. The stepped region can be between about 0.1 to about 0.5 inches, in some embodiments.

Figure 6A:
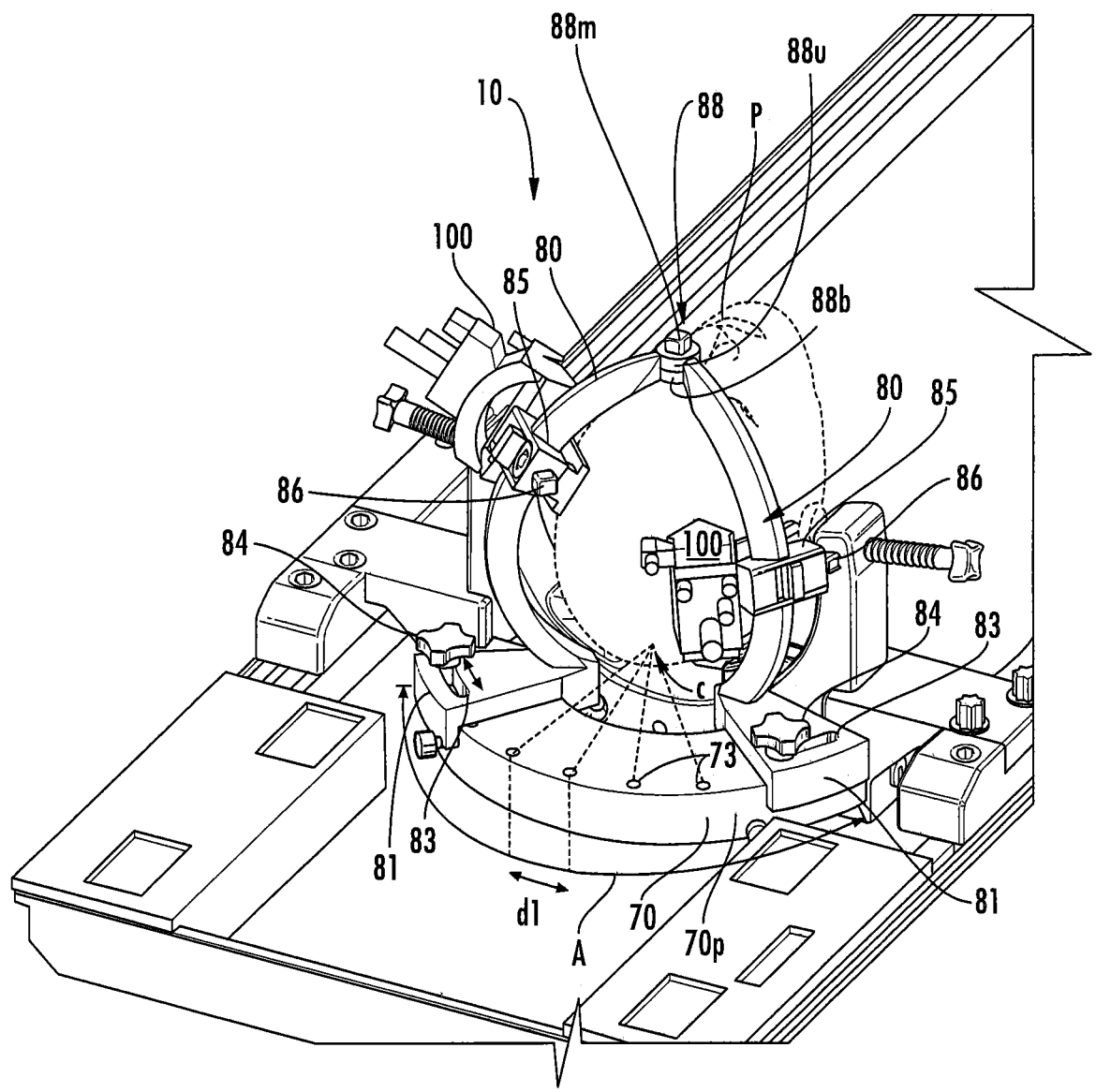
FIG. 6A is an end perspective view of the frame assembly illustrating the frame assembly accommodating two turret arms according to embodiments of the present invention.

Referring to FIG. 6A, the turret base 70 may have an outer perimeter 70p that has an angular distance A that is about 60-180 degrees relative to a center drawn with respect to the arc residing under the patient (in the embodiment shown, under the head). The respective apertures 73 can be symmetrically or asymmetrically positioned. Typically, they are symmetrically spaced circumferentially apart a distance $d_1$, positioned at about 5-20 degrees apart, e.g., about every 5 degrees, 6 degrees, 7 degrees, 8 degrees, 9 degrees, 10 degrees, 12 degrees, 12.5 degrees, 15 degrees or 20 degrees apart.

FIGS. 6A, 6B and 7A, 7C-7G illustrate examples of at least one turret arm 80 that is held by the turret base 70. As shown, the turret base 70 can accommodate a plurality of the turret arms 80. The arms 80 can be curvilinear, shown as having an arcuate body, and can extend up from the turret base 70 to reside over target anatomy of the patient P. Respective turret arms 80 can be supported by a support member 81 that releasably and position-adjustably attaches to the turret base 70. The support member 81 can include an aperture 83 that engages a lock screw 84 to engage an underlying aperture 73 in the base 70. In some embodiments, the aperture 83 can be configured as a circumferentially and/or laterally extending slot. The slot 83 can have a length that may also correspond to $d_1$ and/or is sufficient to overly two adjacent downwardly extending channels/apertures 73. Thus, in some embodiments, the arrangement of the cooperating slot 83 and channel/apertures 73 can allow for a large number (e.g., almost infinite or continuous) lockable positions of the arm 80 over the range of the turret base 70 at least where a single arm 80 is used and over half of the base perimeter when two are used.

The support member 81 can be integral to the turret arm 80. The turret arm 80 and support member 81 may have a unitary molded body.

Figure 6B:
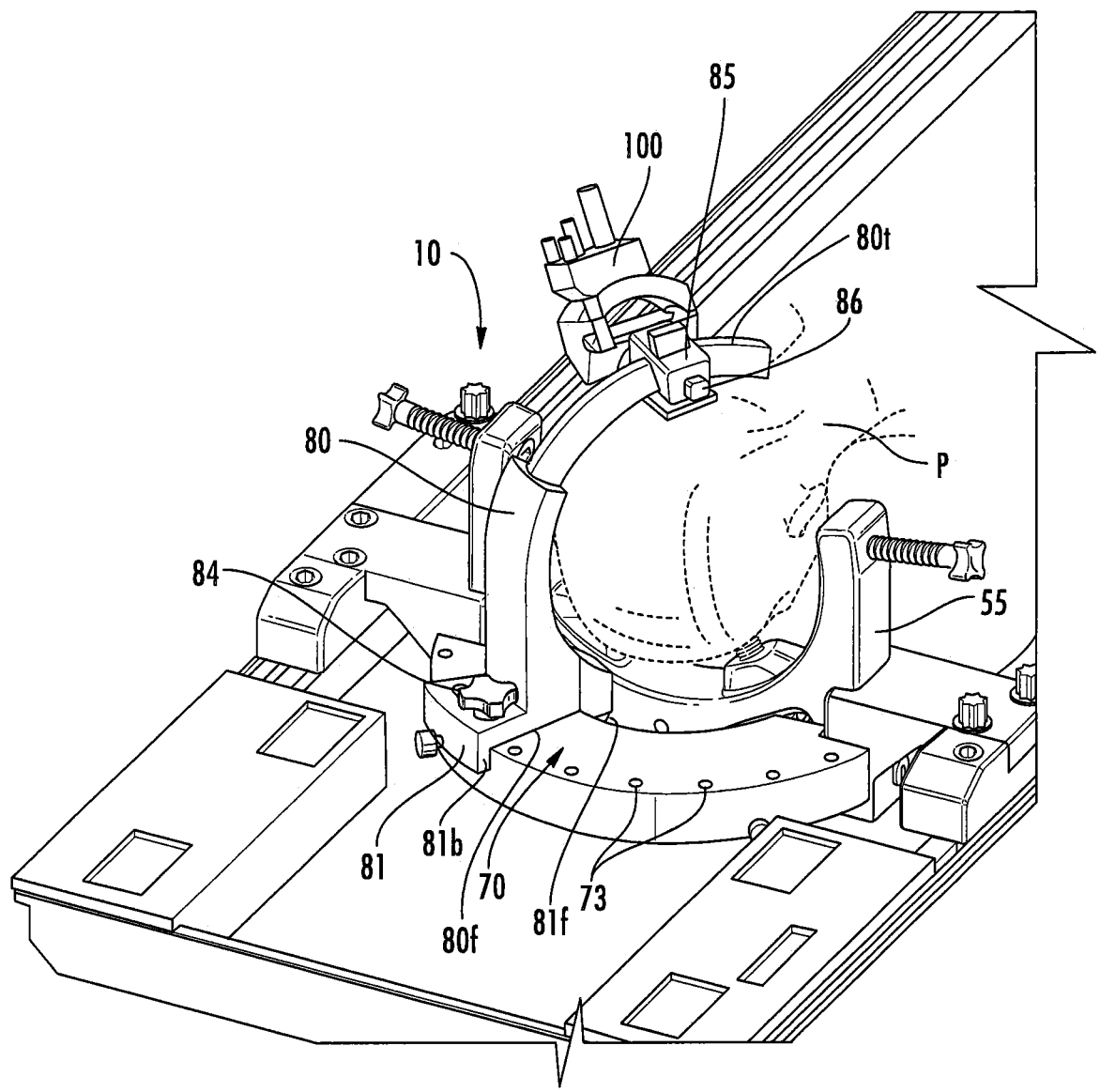
FIG. 6B is an end perspective view of the frame assembly illustrating the frame assembly with a single turret arm according to embodiments of the present invention.

As shown in FIGS. 6B and 7A, for example, the turret arm 80 can have a flat bottom surface 80f that resides on a flat upper surface 78 (FIG. 5B) of the turret base 70. The support member 81 can have a front edge 81f that extends down a distance over the front of the turret base 70 on one side of the flat bottom surface of the turret arm 80. The support member 81 can have a back edge portion 81b that resides above the turret base 70 on the other side of the flat bottom surface 80f (opposing the front edge) and holds the aperture 83 (which can be a laterally extending slot) that aligns with a desired channel 73 in the turret base 70.

The turret arm (s) 80 can rise up above the base 70 and extend inward therefrom a distance sufficient to place the end of the turret arm(s) 80 over a target region of a patient P. The turret arm(s) 80 can have an arcuate segment that extends inward from the base 70 a distance of between about 3-10 inches, more typically between about 4-8 inches, such about 4 inches, about 5 inches, about 6 inches about 7 inches, and about 8 inches, in some embodiments. The turret arm (s) 80 can be non-articulating.

The surgical tool 100 can be attached to the turret arm 80 using at least one mount member 85 that can slidably move over the turret arm 80 to allow for positional adjustment relative thereto. A lock screw, clamp, pin or other locking member 86 can be used to lock the mount member 85 in a desired location on a corresponding turret arm 80.

As shown in FIGS. 6A and 7A, for example, two turret arms 80 can optionally be configured to rise up from the turret base 70 and attach together for additional structural reinforcement. The attachment region can include aligned upper and lower segments 88u, 88b that attach using any suitable attachment configuration such as snap fit, frictional engagement, tongue and groove, rails and channels, VELCRO, screws, pins and the like (shown as with a single threaded member 88m extending through aligned channels in the upper and lower segments 88u, 88b. However, a single arm 80 can be used with the frame assembly 10 (FIG. 6B) and when multiple arms 80 are used they are not required to attach to another arm.

FIG. 6B illustrates another example of a turret arm 80. As shown, the turret arm 80 has a length sufficient to extend over a portion of a head of a patient for brain surgeries. Optionally, the turret arm may 80 can have a telescoping end portion 80t. This configuration may be particularly suitable for an occipital approach using a single, long arm configuration as shown. The telescoping end portion 80t can rise up from a static lower portion as shown. The telescoping end portion 80t can have a length that corresponds to the static lower portion or may be longer or shorter. The telescoping end portion 80t can have a length that is between 2-12 inches, more typically between 4-10 inches, such as about 4 inches, about 5 inches, about 6 inches, about 7 inches, about 8 inches, about 9 inches and about 10 inches, in some embodiments.

The frame assembly 10 can be configured to releasably and interchangeably accommodate different turret arm 80 configurations for different applications.

FIGS. 7A-7G illustrate that the frame assembly 10 can have one or more turret arms 80 (shown as two), typically with arcuate segments and one or both of which can have curvilinear (e.g., arcuate) upwardly extending channels 80c. The channel 80c can be through-channels or closed channels (e.g., recesses) that extend over at least a major portion of a length of the arm 80, typically between about 2-12 inches, such as 2 inches, 3 inches, 4 inches, 5 inches, 6 inches, 7 inches, 8 inches, 9 inches, 10 inches, for example.

Figure 7B:
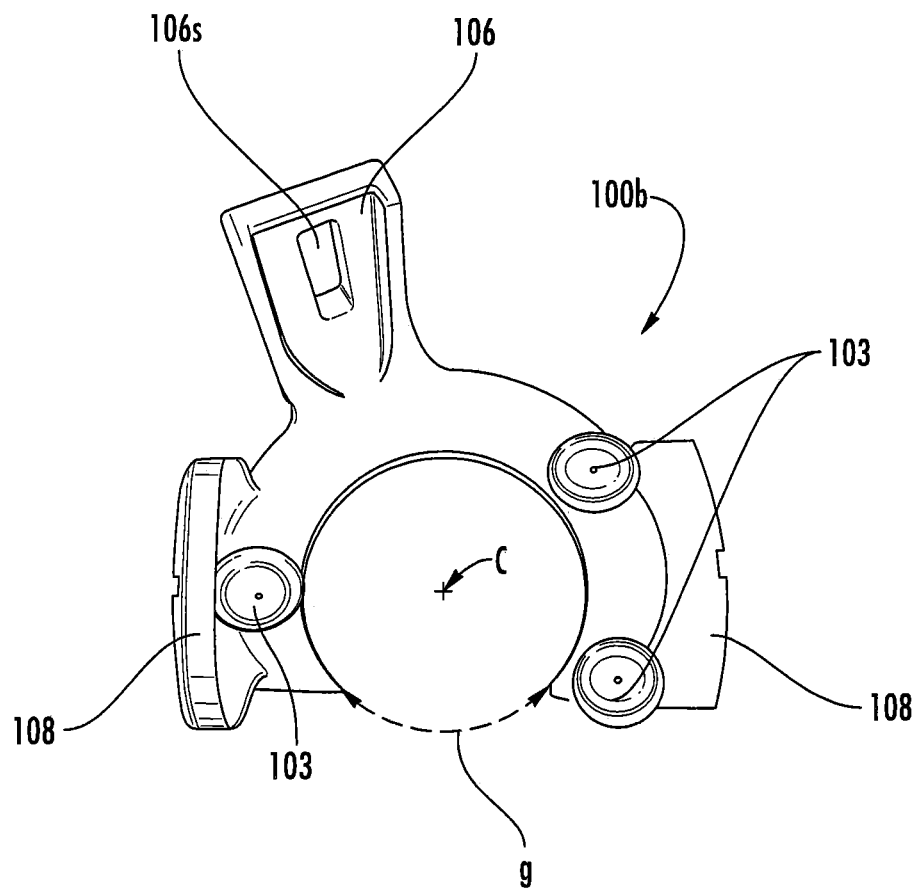
FIG. 7B is an enlarged top perspective view of a base that holds a surgical tool that can attach to the turret arm of the frame assembly according to embodiments of the present invention.
Figure 7C:
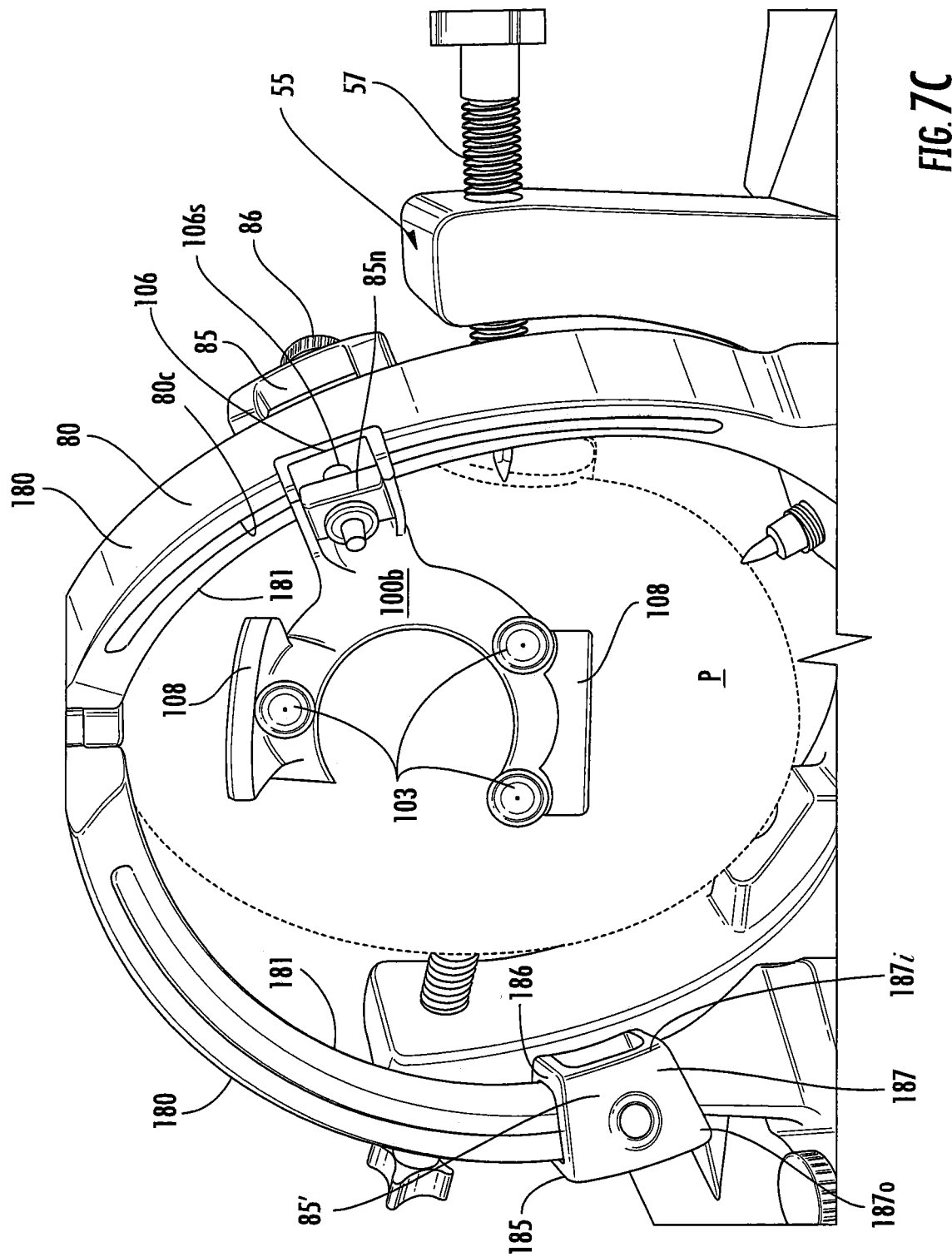
FIG. 7C is a side perspective view of the frame assembly shown in FIG. 7A.

Referring to FIG. 7C, the turret arm(s) 80 can have parallel, substantially planar, parallel inner and outer surfaces or walls 180, 181 with the recess or through-channel 80c residing therebetween. The outer surface or wall 180 can be wider than the inner surface or inner wall 181.

Referring to FIG. 7C, in some embodiments, the mount member 85' (the one shown on the left side of the figure) can have a polygonal shape with four spaced apart walls, two sidewalls 187 connecting the inner and outer walls 185, 186, The sidewalls 187 can angle/taper in one direction, typically inward, so that the sidewall has a greater dimension on one corner relative to the other corner, typically the outer corner 187o relative to the inner corner 187i.

Still referring to FIG. 7C, in some embodiments, the mount member 85 (the one shown on the right side of the figure) can be provided as two separate cooperating components, the outer component that resides against an outer wall 180 of the turret arm 80 and an inner (nut-like) component 85n that can reside against a mounting arm 106 of the base 100b over the slot 106s.

The turret base 70 can include a plurality of spaced apart apertures 73 that engage the locking member 84, allowing different positional placements of a respective turret support member 81 relative to the base 70 and patient P. Where two turret arms 80 are used, as shown, they can be attached at a top end via attachment member 88m. The two arms 80 can be attached at an upper end portion. As shown, the arms 80 have aligned upper end segments forming upper and lower portions 88u, 88b of an attachment joint.

FIG. 7B illustrates an example of a support base 100b that can be used to hold the tool 100. The base 100b can include an outwardly extending turret attachment arm 106. The turret attachment arm 106 of the base 100b can include a slot 106s. The base 100b can also include a plurality of fiducials 103. The base 100b can have a perimeter that is discontinuous, e.g., it partially surrounds a center C that is the target for a patient entry site (a burr hole in the skull in some embodiments) so that it has a gap or open region g along one side, typically between about 20-180 degrees, more typically the gap g is between about 60 to about 145 degrees. The gap g can face the other turret arm 80 (the one not supporting the base 100b), where a second turret arm is used, as shown in FIGS. 7C-7E.

As shown in FIG. 7C, the base 100b can have opposing arcuate arms 108 and the turret attachment arm 106 can reside between the opposing arcuate arms 108. The turret attachment arm 106 can reside closer to one arcuate arm 108 than the opposing arcuate arm 108. The arcuate arms 108 can attach to a tower structure with an X-Y table holding the targeting cannula ("TC") or guide member 100g (FIG. 7D) and can allow positional adjustment of the TC and/or guide member.

As also shown in FIG. 7C, a mount member 85 can engage the base attachment arm 106 and can secure the base 100b to the turret arm 80 using the locking member 86. The mount member 85 can reside on one side of the channel 80c and the arm 106 on the other with the locking member 86 extending through the channel 80c. The mount member 85 can have an outer ledge that rests against an outer surface of the turret arm 80.

Referring to FIGS. 7A and 7C, the left side arm 80 is shown with the channel 80c formed as an elongate recess or groove while the right side arm 80 is shown with a open through-channel or open slot 80c. However, other arm configurations may be used not requiring an open slot or recessed slot (e.g., FIG. 1). Although there are two different exemplary types of arcuate arms 80 shown in FIGS. 7A and 7C, the assembly 10 may use only one type or both types. It is also contemplated that the arm 80 can have other configurations. The mount members 85, 85' can act as an adjusting mechanism and positional lock/clamp for the corresponding configuration of the arm 80.

It is contemplated that one can use a single turret arm 80 (unilateral case) or dual turret arms 80 (bilateral case) for neurological, e.g., brain surgeries or other target anatomical locations using an appropriate arm (arc) design. More than two arms 80 may be used for other anatomical targets or other surgical interventions.

FIGS. 7D and 7E illustrate that the turret arm 80 and base 100b can releasably engage or attach to cooperate to position the tool 100 at different heights.

Figure 7F:
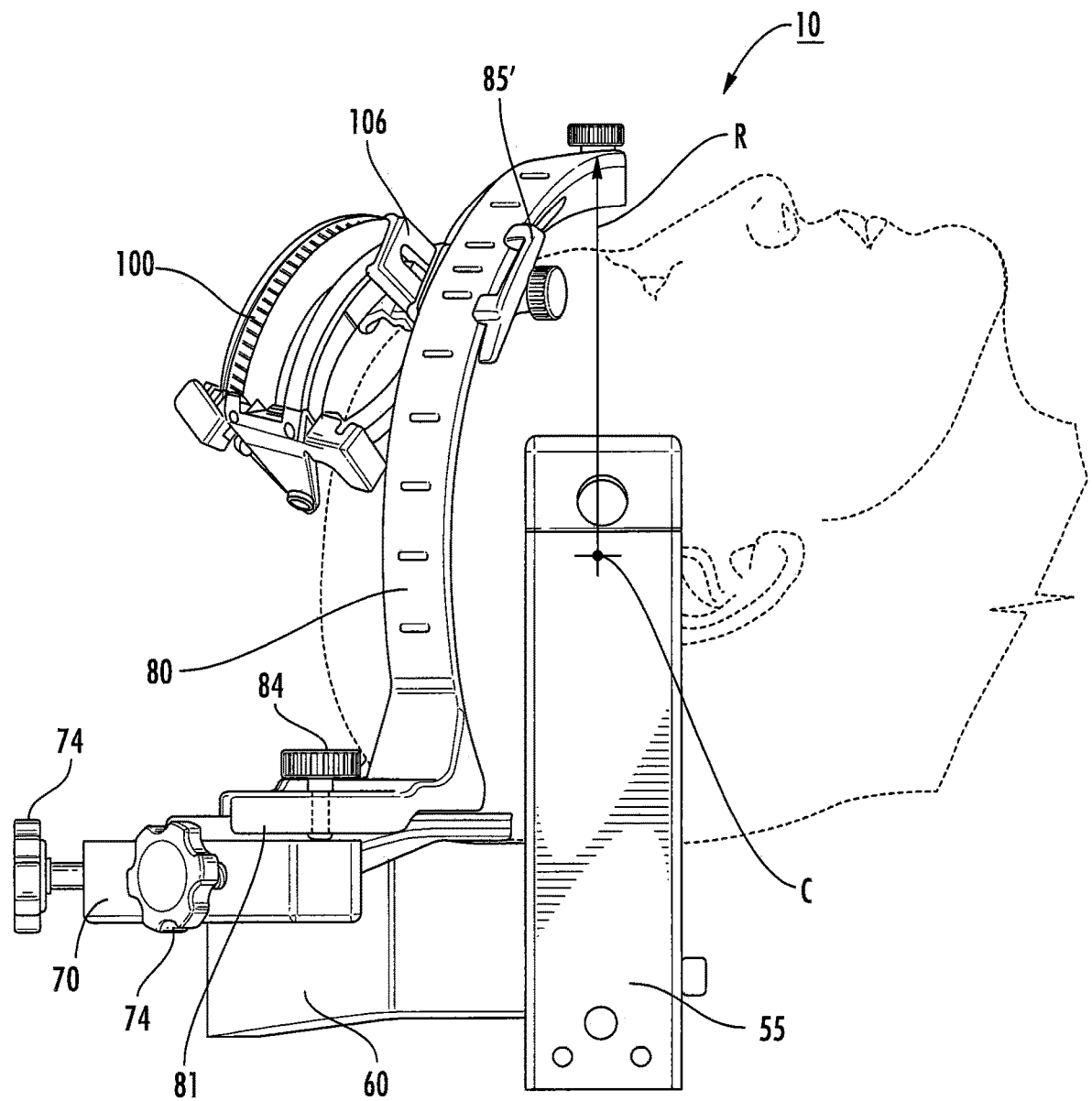
FIGS. 7F and G are side perspective view of the frame assembly shown in FIG. 7A illustrating alternate locations of a respective turret arm and a radius of curvature according to embodiments of the present invention.
Figure 7G:
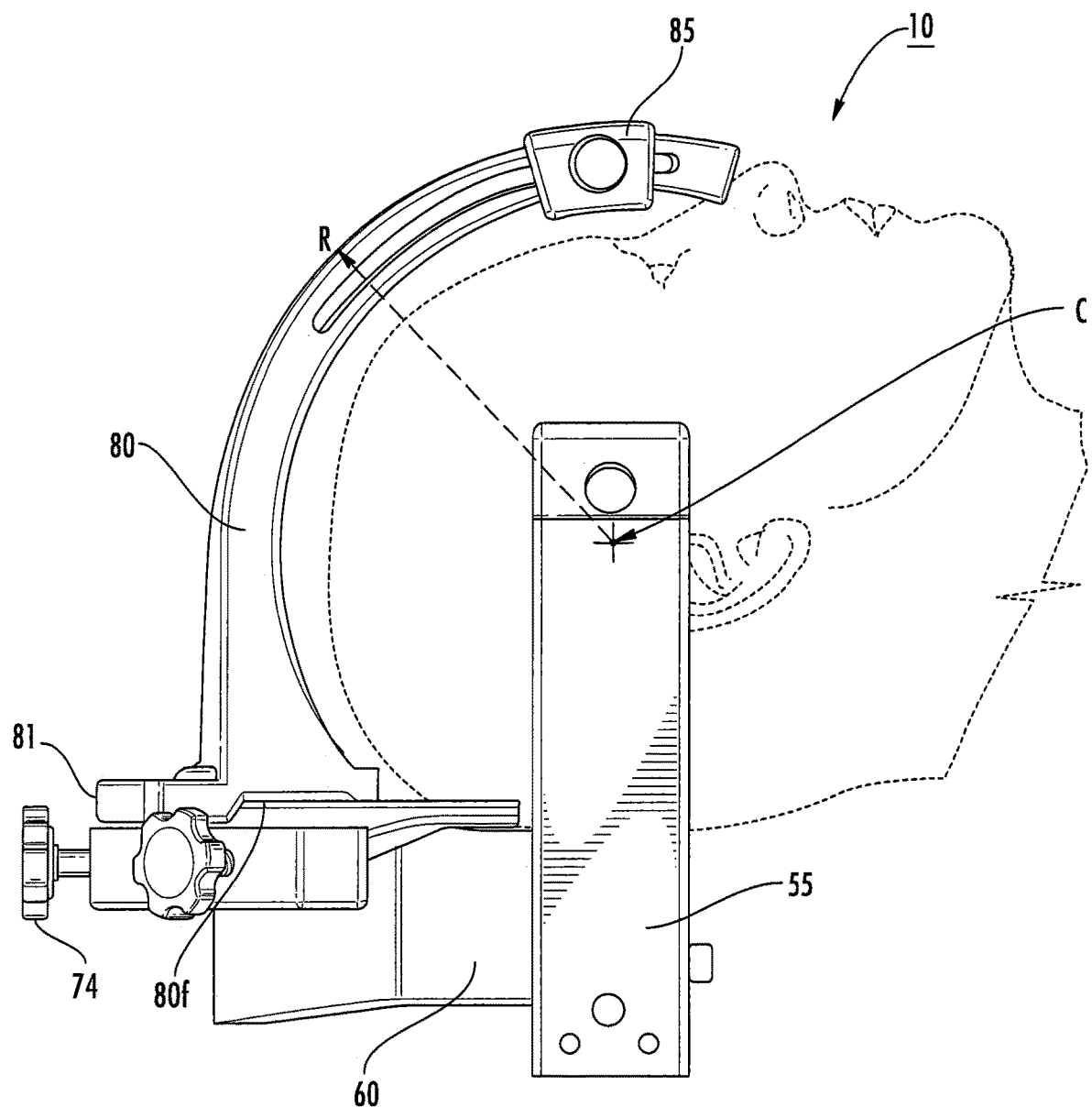
FIG. 7A is an end perspective view of a frame assembly according to embodiments of the present invention.
FIGS. 7D and 7E are end, partial side perspective views of the frame assembly shown in FIG. 7A illustrating different exemplary positions of the guide or targeting cannula on a turret arm of the frame assembly according to embodiments of the present invention.

FIGS. 7F and 7G illustrate that the turret arm 80 can have a radius of curvature R measured from a center C of a x, y, z, coordinate system that is projected to be over a target anatomical position, shown as a depth in a skull of a patient P. In some embodiments, the center C is aligned with a deep brain region of the patient P, behind and above the ear, below the eye socket, as shown. In some embodiments, the turret arm 80 can have an arcuate segment with a radius of curvature that is between 100 mm and 150 mm, typically between about 110 mm and 140 mm, such as about 110 mm, about 120 mm, about 130 mm, and about 140 mm. In some particular embodiments, the arm 80 can have a curvature that is between 135 mm and 136 mm. Where more than one arcuate arm 80 is used, they can have the same radius of curvature R or a different radius of curvature R.

The turret arm 80 and turret base 70 can be configured to be reusable and the base 100b can be single-use disposable.

Figure 8:
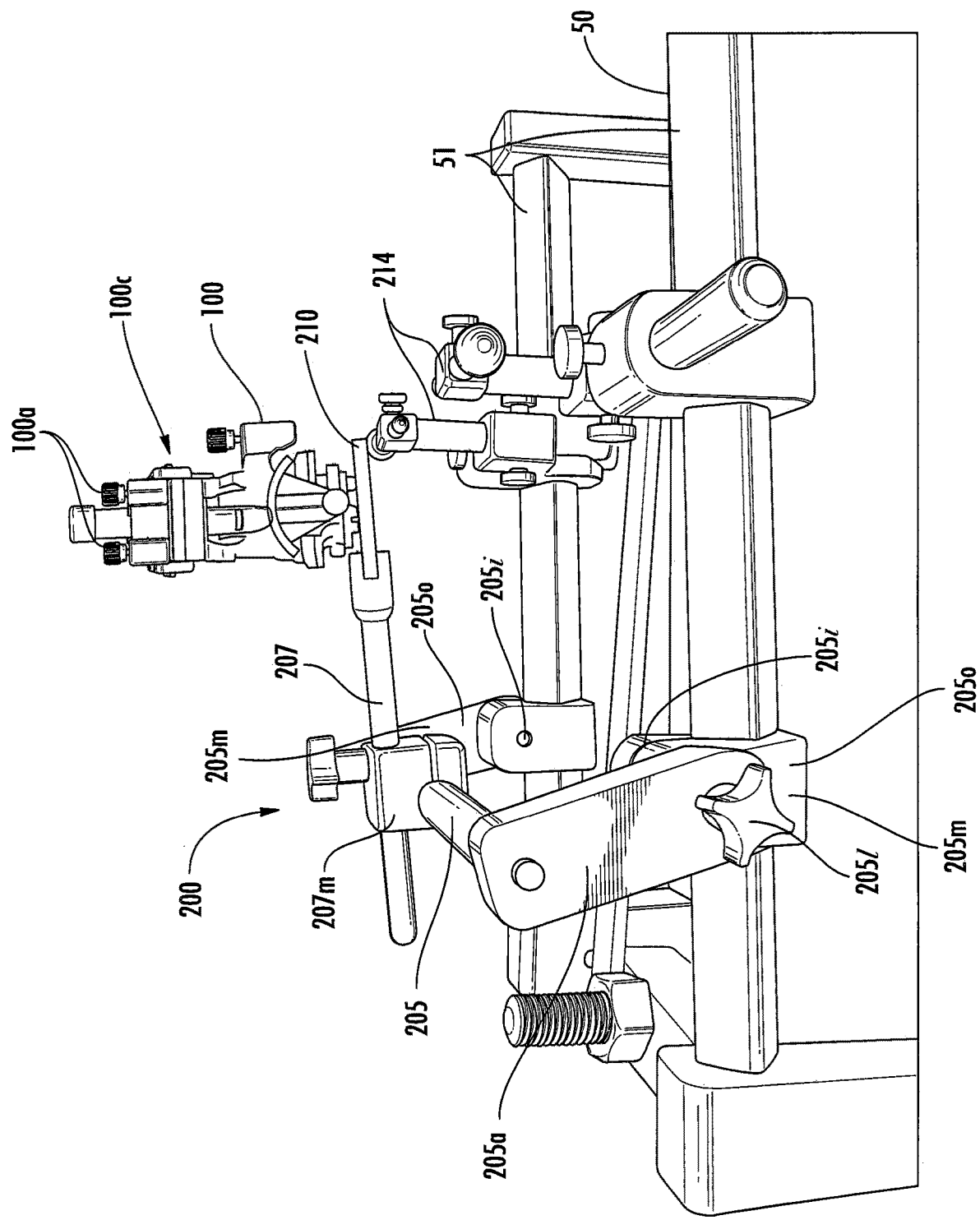
FIG. 8 is a side view of another surgical positioning device according to yet other embodiments of the present invention.
Figure 9:
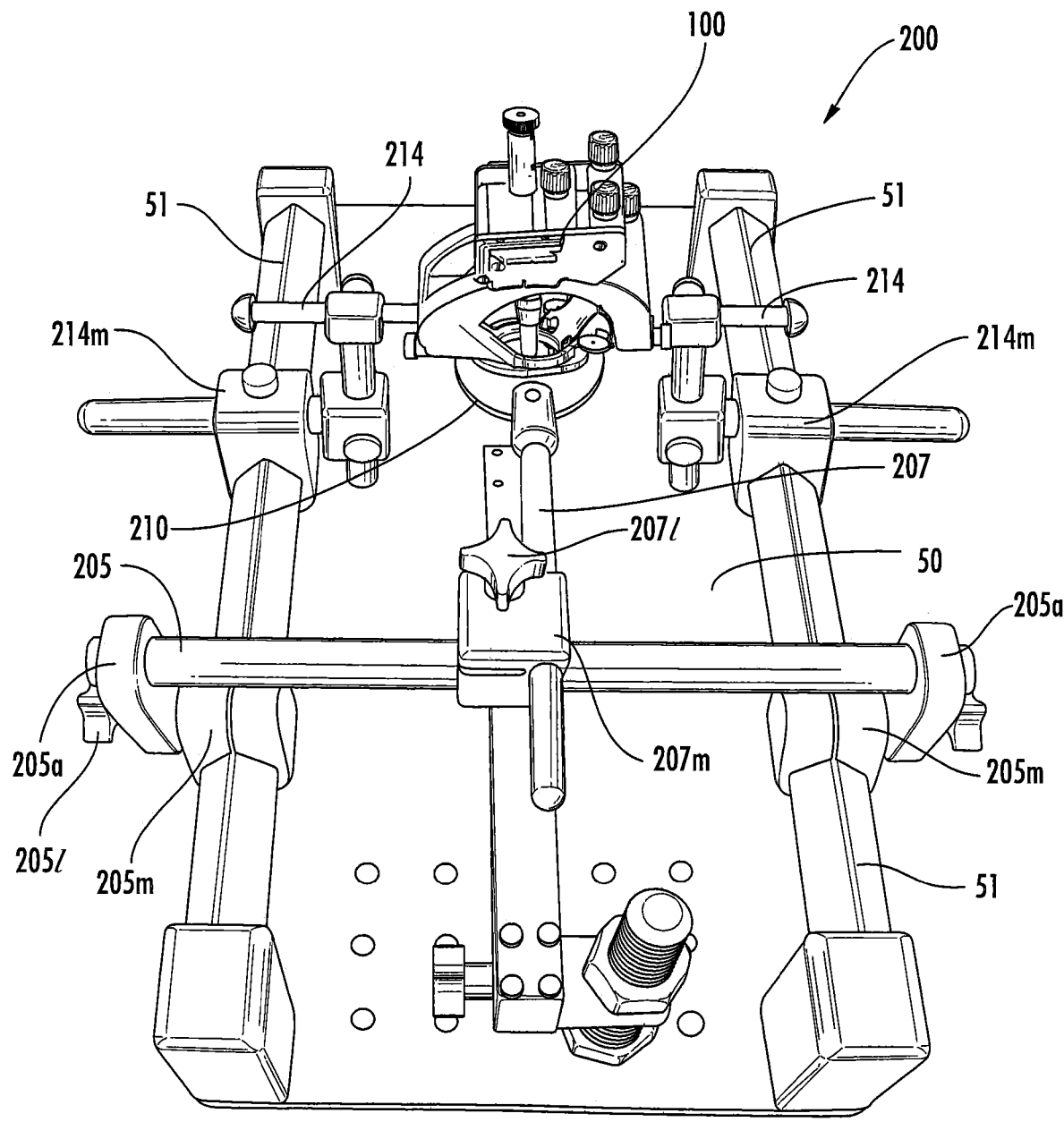
FIG. 9 is a top view of the device shown in FIG. 8.
Figure 10:
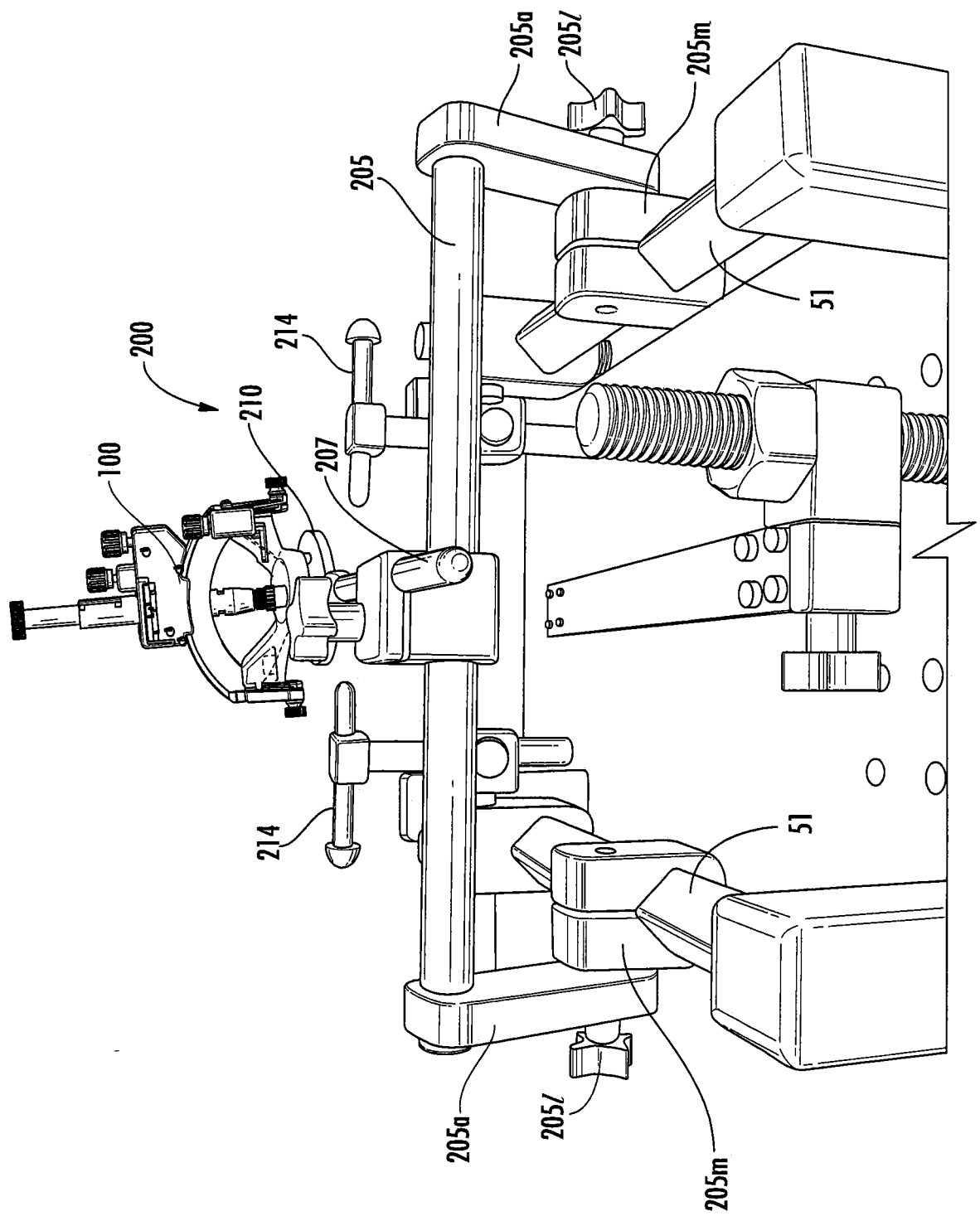
FIG. 10 is an end perspective view of the device shown in FIGS. 8 and 9.
Figure 11:
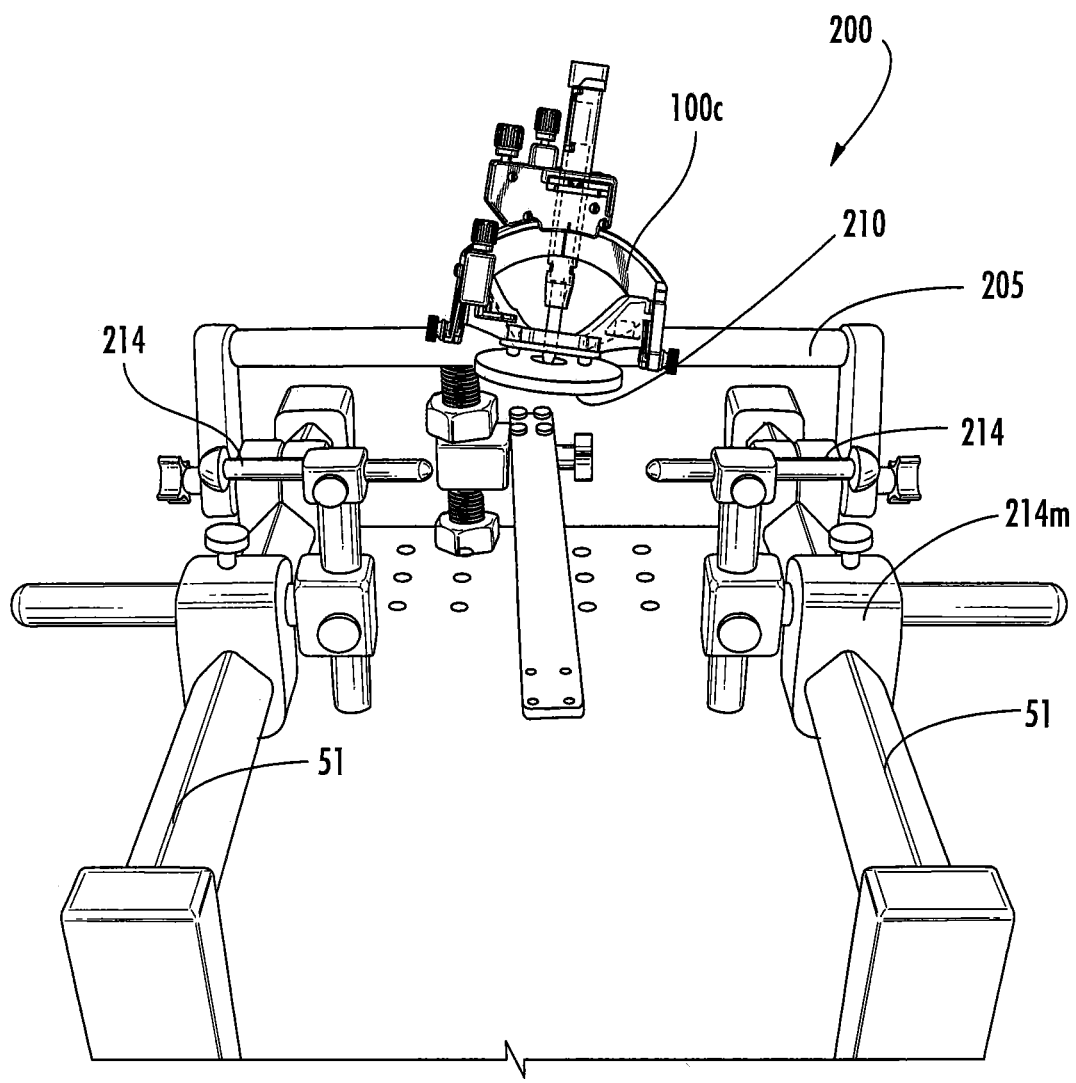
FIG. 11 is an end perspective view of the device shown in FIGS. 8 and 9, opposite the view shown in FIG. 10.

FIGS. 8-11 illustrate another embodiment of a surgical positioning assembly 200. As shown, the assembly 200 attaches to longitudinally extending scanner table rails 51. The assembly 200 includes a laterally extending cross member 205 that is pivotably attached to the rails 51 via arms 205a and mounting members 205m with locks 205l. FIG. 8 illustrates the arms 205a pivoted and lockingly attached to the siderails 51 to be angled from vertical for positional adjustment. The mounting members 205m can have inner and outer cooperating components 205i, 205o (FIG. 8) that engage opposite sides of the rails 51 and allow the arm 205a to pivot relative to the rails 51 for positional (e.g., height) adjustment of the member 210.

FIGS. 8-11 illustrate that the cross-member 205 holds a longitudinally extending rod 207. The cross-member 205 includes a locking device 207m that allows the rod 207 to slide a distance longitudinally in fore and aft directions and lock into position with lock 207l. Sliding lateral adjustment of the rod 207 relative to the cross bar 205 is also contemplated.

Embodiments shown in FIGS. 8-11 may be particularly suitable for use in procedures that have soft tissue intrabody entry sites which lack sufficient structural rigidity to either support a tool in a desired position and/or to maintain a defined trajectory path to the intrabody target site.

The rod 207 holds the surgical tool 100. As shown, the rod 207 is attached to a holding member shown as a plate 210 with an aperture that holds the tool 100, shown as a targeting cannula or guide 100c.

The assembly 200 can also include a pair of fixation members 214 that mount to the respective rails 51 via clamping members 214m a distance away from the cross-member 207, typically closer to the surgical tool 100. The members 214 can be laterally adjustable for position. The members 214 can be skull fixation members that are adjustable to accommodate different size heads, for example.

The frame assembly 10 and/or surgical positioning assembly 200 can be sized and configured to fit within the bounds of a bore 50b of a magnet (for closed bore systems) and can translate in and out of the magnet bore with the patient and scanner bed 50 and remain in a fixed position relative to the patient.

Components of the frame assembly 10 and/or positioning device 200 can be formed from any suitable material, typically a light-weight relatively rigid polymeric material, such as, for example, fiberglass, ceramics, fiber reinforced resins, PEEK, ABS, polycarbonate, KEVLAR, and/or Garolite. However, non-ferromagnetic metals or other materials may also be used, particularly when used for non-MRI surgical navigation systems.

The devices 10 and/or 200 may be particularly suitable for use in MRI-guided procedures where the procedure is carried out in an MRI scanner or MRI interventional suite, e.g., deep brain procedures, spinal procedures, cardiac procedures, including but not limited to, cardiac EP procedures where heat or cryogenic ablation is used, as well as intrabody biopsies or treatment of any target organ or tissue, including breast, liver, thyroid, lung, kidney, ovarian, cervical, prostate, urethra, colon, intestine, stomach, and the like. The devices be suitable for MRI-guided procedures that deliver therapeutic agents, such as drugs, antigen, antibody and/or gene therapies, stem cells and the like. However, use in non-MRI image guided systems are also contemplated.

The frame assembly 10 and/or positioning assembly 200 (or appropriate components of one or both, depending on use) can be sterilized and may optionally be single-use disposable or portions thereof may be single-use disposable. The devices can be "universal" in that one or both can be used interchangeably with different MRI scanner systems from different scanner manufacturers. Alternatively, the frame assembly 10 and/or positioning assembly 200 may have different configurations of the attachment members used to attach to different Scanner beds, e.g., they may be scanner type or scanner manufacturer specific.

The surgical tool can comprise a trajectory assembly that includes the targeting cannula 100c on a frame with a platform for X-Y adjustment, and actuators 100a (FIG. 8) that can adjust the pitch, roll and X-Y adjustments of the trajectory. The frame can include at least one fiducial marker. For additional discussion of suitable trajectory guides, see, U.S. application Ser. No. 12/134,412, and co-pending, co-assigned U.S. patent application Ser. Nos. 12/236,950, and 14/515,105, the contents of which are hereby incorporated by reference as if recited in full herein.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A surgical frame assembly comprising:
    a turret base, wherein, in use, the turret base rests on a support surface adjacent to but longitudinally spaced apart from a patient and the turret base comprises downwardly extending spaced apart inner and outer arcuate perimeters and a planar upper surface with a plurality of circumferentially spaced apart downwardly extending apertures, wherein the turret base comprises an internal arcuate and downwardly extending open channel that is under the upper surface and between the downwardly extending spaced apart inner and outer arcuate perimeters;
    at least one turret arm comprising opposing first and second end portions with an arcuate segment therebetween, wherein the first end portion terminates above the second end portion and above the turret base, wherein the second end portion comprises a front lower edge that extends forward of and down a distance over the inner arcuate perimeter of the turret base, wherein the second end portion further comprises a horizontally oriented planar lower end portion that is attachable to the turret base, wherein the second end portion extends a distance below the arcuate segment, wherein the horizontally oriented planar lower end portion comprises a laterally extending slot with a laterally extending length dimension that is greater than a height dimension thereof and that resides over a plurality of the circumferentially spaced apart apertures of the turret base, wherein the at least one turret arm has a unitary body with the arcuate segment merging into the second end portion with the front lower edge and the horizontally oriented planar lower end portion, and wherein the at least one turret arm is configured to place the arcuate segment above the turret base;
    a vertically extending lock screw extending through the slot into one of the downwardly extending apertures, wherein the at least one turret arm is lockable into different positions relative to the turret base using different ones of the downwardly extending apertures and the lock screw; and
    a surgical tool moveably attached to the arcuate segment of the at least one turret arm so that the surgical tool is positionally adjustable relative to a target anatomical location of a patient under the arcuate segment of the at least one turret arm.

2. The frame assembly of claim 1, wherein the surgical tool is or is held by a trajectory guide comprising a trajectory guide base with a turret attachment arm defining an elongate slot, wherein the turret attachment arm extends perpendicular from a semi-circular base portion of the trajectory guide base and resides closer to a respective turret arm than other portions of the trajectory guide base, wherein the semi-circular base portion comprises first and second spaced apart arcuate arms and a plurality of spaced apart fiducials, and wherein a mounting member extends through the elongate slot of the turret attachment arm of the trajectory guide base to attach the trajectory guide to the arcuate segment of the one turret arm of the at least one turret arm so that the trajectory guide is positionally adjustable relative to a patient in X, Y and Z directions.

3. The frame assembly of claim 1, wherein the surgical tool comprises a trajectory guide with a base comprising a semi-circular perimeter surrounding an open center portion with first and second neighboring base perimeter segments that are arcuate and that are spaced apart from each other, and wherein the trajectory guide is slidably attached to the at least one turret arm so that the trajectory guide is slidably positionable at different radial positions over a length of the arcuate segment of the turret arm.

4. The frame assembly of claim 1, wherein the arcuate segment of the at least one turret arm has a radius of curvature, measured from a centerline of a center aligned with a deep brain region of a patient, behind and above an ear and below an eye socket, that is between about 100 mm and 150 mm.

5. The frame assembly of claim 1, wherein the arcuate segment of the at least one turret arm comprises an arcuate elongate channel residing between upper and lower outer surfaces of the arcuate segment of the at least one turret arm, wherein the arcuate segment of the at least one turret arm comprises first and second sidewalls that join the upper and lower outer surfaces and that provide the arcuate elongate channel over a sub-length thereof, wherein the frame assembly further comprises and a mounting member that has four joined walls that define an open center channel, and an attachment screw that extends through one of the four walls to secure the surgical tool to the mounting member and the at least one turret arm, wherein the open center channel slidably receives one turret arm of the at least one turret arm, and wherein a first wall of the four joined walls faces the first sidewall of the one turret arm, a second wall of the four joined walls faces the second sidewall of the one turret arm, a third wall of the four joined walls faces the upper outer surface of the one turret arm and a fourth wall of the four joined walls faces the lower outer surface of the one turret arm.

6. The frame assembly of claim 1, wherein the at least one turret arm includes first and second spaced apart turret arms concurrently held by the turret base, wherein the first and second turret arms have a common size and shape and the planar lower end portion of each is directly attached to the turret base at circumferentially spaced apart locations, and wherein the first and second turret arms are each coupled to different trajectory guides as the surgical tool that is moveably attached to the arcuate segment and each trajectory guide is positionally adjustable relative to different target anatomical locations of a patient under the arcuate segment of the first and second turrent arms.

7. The frame assembly of claim 6, wherein the first end portion of each of the first and second turret arms are attachable to each other via aligned vertically oriented upper and lower channels that reside at a tip of the first and second turret arms above the arcuate segments, and wherein a downwardly extending fastener extends through the upper and lower channels to thereby attach the first end portions of the first and second turret arms.

8. The frame assembly of claim 1, wherein the arcuate segment of the at least one turret arm has a telescoping configuration such that that the arcuate segment has an end that can extend and retract from a lower portion of the turret arm to reside at different height positions.

9. The frame assembly of claim 1, further comprising a mount member attached to the arcuate segment of the at least one turret arm, wherein the mount member is slidably extendable over the arcuate segment and securely attaches the surgical tool at a desired location selectable over a at least a major portion of a length of the arcuate segment of the at least one turret arm, wherein the mount member comprises an open center channel that slidably receives one turret arm of the at least one turret arm, and wherein the open center channel has a cross-sectional shape that has two long sides and two shorter sides.

10. The frame assembly of claim 1, further comprising a hoop mount attached to a head fixation frame, wherein the hoop mount is arcuate and comprises vertically oriented arcuate inner and outer walls, and wherein the hoop mount is also attached to the turret base with the internal arcuate channel of the turret base receiving the hoop mount, wherein head fixation members of the head fixation frame extend laterally inward on opposing sides of the head fixation frame, wherein the arcuate segment of the at least one turret arm extends above the head fixation members at a location that is proximate the head fixation members so as to reside over a head of a patient, and wherein the turret base further comprises a plurality of radially extending apertures extending through the downwardly extending outer perimeter with attachment members extending therein configured to secure the turret base to the hoop mount in a fixed position.

11. The frame assembly of claim 2, wherein the semi-circular base portion of the base of the trajectory guide has a center opening overlying a target intrabody entry point of a patient.

12. The frame assembly of claim 1, wherein the second end portion of the at least one turret arm comprises a recess between the front lower edge and the horizontally oriented planar lower end portion with the laterally extending slot, wherein the recess is sized and configured to receive the upper surface of the turret base, and wherein the downwardly extending apertures are cylindrical apertures.

13. The frame assembly of claim 1, wherein the at least one turret arm comprises first and second turret arms, wherein the first and second turret arms are non-articulating, wherein the lower end portions of the first and second turret arms are independently moveably attachable at different locations of the turret base, and wherein the first and second turret arms have a common size and shape and the planar lower end portion of each is directly attached to the turret base at circumferentially spaced apart locations.

14. The frame assembly of claim 1, further comprising:
a surgical tool base that holds the surgical tool, the surgical tool base having a planar bottom surface with an inner perimeter that is semi-circular and surrounds an open center, wherein the planar bottom surface merges into an outwardly extending turret connection arm that is perpendicular to the planar bottom surface and that extends off an outer perimeter segment of the planar bottom surface to reside closer to the turret arm than the planar bottom surface; and
a mount member that attaches the turret connection arm to a respective at least one turret arm to hold the surgical tool base at a desired height location, adjustable relative to the corresponding turret arm, wherein the mount member comprises a first coupling member which abuts a first sidewall of one turret arm of the at least one turret arm, an inner nut that abuts the turret connection arm which abuts a second sidewall of the one turret arm, and a fixation screw that extends through the first coupling member, the turret connection arm and the nut to secure the surgical tool base to the mount member.

15. The frame assembly of claim 14, wherein the inner perimeter of the surgical tool base has a circumferentially extending gap space having an angular extent that is in a range of about 60 degrees to 145 degrees that positions neighboring segments apart from each other, wherein the neighboring segments each comprise an upwardly extending arcuate arm, and wherein the surgical tool base holds a plurality of circumferentially spaced apart fiducials.

16. The frame assembly of claim 1, wherein the slot length dimension is greater than a separation distance between adjacent ones of the downwardly extending apertures of the turret base to thereby allow for various lockable positions.

17. A method of preparing for an image-guided surgery, comprising:
providing a head fixation assembly;
attaching a laterally extending hoop mount to the head fixation assembly, wherein the hoop mount is vertically oriented and is arcuate;
attaching a turret base to the hoop mount by placing an arcuate downwardly extending internal and vertically oriented channel of the turret base onto the hoop mount to receive the hoop mount which holds the turret base above a patient support surface, wherein, in use, the arcuate downwardly extending internal and vertically oriented channel is under a flat upper surface of the turret base and resides between first and second vertically oriented arcuate perimeters, and wherein the hoop mount, the turret base and the internal channel are semi-circular and span a width sufficient to surround a head of a patient; then
attaching a lower end portion of at least one turret arm directly to the turret base, wherein the at least one turret arm has a unitary body with an arcuate segment merging into the lower end portion, and wherein the arcuate segment extends above the turret base and terminates at an upper free end portion of the turret arm;
adjusting a location of the at least one turret arm relative to the turret base to a desired position relative to a patient's head, wherein the turret base comprises a plurality of circumferentially spaced apart downwardly extending vertically oriented apertures, wherein the turret arm has an arcuate slot in a lower horizontally oriented portion of the turret arm, wherein the slot comprises a length in a lateral extent that is greater than a width and that is greater than a separation distance between adjacent ones of the plurality of downwardly extending apertures in the turret base, wherein the adjusting the location of the at least one turret arm is carried out by aligning the slot over a selected one of the downwardly extending apertures in the turret base and tightening a lock screw against the slot and into the selected one of the downwardly extending apertures; and attaching a surgical tool to the turret arm.

18. The method of claim 17, wherein the surgical tool comprises a trajectory guide with a primary body with an open cylindrical channel and a trajectory guide base that is releasably attachable to the trajectory guide, wherein the at least one turret arm comprises an arcuate elongate channel extending along a length of the at least one turret arm, and wherein the method further comprises adjusting a height of the trajectory guide base relative to the arcuate segment of the turret arm before attaching the trajectory guide primary body, wherein the trajectory guide base comprises an attachment arm with an upwardly extending and elongate slot that is parallel to a sidewall of the turret arm under a closed outer surface of the arcuate segment of the turret arm, the attachment arm extending perpendicular to a planar semi-circular bottom of the trajectory guide base, wherein the semi-circular bottom resides under the attachment arm with the elongate slot and projects outwardly away from the attachment arm and turret arm toward the patient with the attachment arm residing closer to the turret arm than the planar semi-circular bottom, wherein the planar semi-circular bottom comprises an inner perimeter extending about an open center portion with first and second neighboring base perimeter segments that are circumferentially spaced apart from each other a distance of between 20-180 degrees, wherein each of the first and second neighboring perimeter segments comprise an upwardly projecting arcuate arm, and wherein, in use, the planar semi-circular bottom does not contact a patient.

19. A surgical frame assembly comprising:
a hoop mount comprising an arcuate body;
a turret base, wherein, in use, the turret base comprises an upper surface, downwardly extending, substantially vertically oriented and arcuate inner and outer perimeters, and an arcuate downwardly extending internal channel, wherein the upper surface comprises a plurality of circumferentially spaced apart downwardly extending apertures, wherein the arcuate downwardly extending internal channel is under the upper surface and between the arcuate inner and outer perimeters and is sized and configured to slidably receive the hoop mount, and wherein the downwardly extending outer perimeter of the turret base further comprises a plurality of radially extending apertures that are orthogonal to the downwardly extending apertures and that cooperate with a respective attachment member that extends therein to secure the turret base to the hoop mount in a fixed orientation; and at least one turret arm comprising an arcuate segment attachable to the turret base, wherein the at least one turret arm comprises a single horizontally oriented planar lower end portion that extends a distance away from the arcuate segment and comprises a laterally extending and arcuate slot with a laterally extending length dimension that is greater than a height dimension thereof and that is capable of residing over two adjacent apertures of the plurality of the circumferentially spaced apart apertures of the turret base, wherein the arcuate segment extends above the turret base, wherein the horizontally oriented planar lower end portion abuts the turret base, and wherein the at least one turret arm has a unitary body with the arcuate segment merging into the horizontally oriented planar lower end portion.

20. The assembly of claim 19, further comprising a fastener extending through the slot into one of the downwardly extending apertures, wherein the at least one turret arm can be locked into different positions relative to the turret base using different ones of the downwardly extending apertures and the fastener, and wherein the turret arm terminates at an upper free end that resides above the turret base.

21. The assembly of claim 19, wherein the hoop mount and the base are semi-circular and configured to reside longitudinally spaced apart from and at a level that is under a head of a patient, wherein the at least one turret arm includes first and second spaced apart turret arms concurrently held by the turret base and each projecting forward toward a nose of a patient, wherein the first and second turret arms have a common size and shape and the horizontally oriented planar lower end portion of each is directly attached to the turret base at circumferentially spaced apart locations, and wherein upper end portions of the first and second turret arms are free ends that are attachable to each other via aligned vertically oriented upper and lower channels and a downwardly extending fastener, and wherein the first and second turret arms are devoid of head fixation pins.

22. The assembly of claim 19, wherein the planar lower end portion of the turret arm resides directly on a flat surface of the upper surface of the turret base, wherein the downwardly extending apertures are cylindrical apertures, wherein the flat surface of the upper surface of the turret base is a closed surface that extends over the downwardly extending internal channel, wherein the turret base, the hoop mount and the downwardly extending internal channel have a semi-circular shape, and wherein the downwardly extending internal channel is open in a direction facing a bottom of the turret base under the flat surface.

* * * * *